US009006738B2

(12) United States Patent
Merz

(10) Patent No.: US 9,006,738 B2
(45) Date of Patent: Apr. 14, 2015

(54) REDUCING CAPACITIVE CHARGING IN ELECTRONIC DEVICES

(75) Inventor: Matthias Merz, Leuven (BE)

(73) Assignee: NXP, B.V., Eindhoven (NL)

( * ) Notice: Subject to any disclaimer, the term of this patent is extended or adjusted under 35 U.S.C. 154(b) by 333 days.

(21) Appl. No.: 13/060,949

(22) PCT Filed: Jul. 21, 2009

(86) PCT No.: PCT/IB2009/053148
§ 371 (c)(1),
(2), (4) Date: Feb. 25, 2011

(87) PCT Pub. No.: WO2010/023569
PCT Pub. Date: Mar. 4, 2010

(65) Prior Publication Data
US 2011/0156177 A1    Jun. 30, 2011

(30) Foreign Application Priority Data

Aug. 25, 2008  (EP) .................................... 08105116
Aug. 25, 2008  (EP) .................................... 08105117
Jul. 21, 2009   (WO) .................. PCT/IB2009/053148

(51) Int. Cl.
*H01L 29/66* (2006.01)
*G01N 27/414* (2006.01)

(52) U.S. Cl.
CPC ........ *G01N 27/4148* (2013.01); *G01N 27/4145* (2013.01)

(58) Field of Classification Search
USPC ................................................... 257/414, 48
See application file for complete search history.

(56) References Cited

U.S. PATENT DOCUMENTS 3,924,175 A * 12/1975 Wilson .......................... 324/444
4,814,059 A *  3/1989 Nishizawa et al. ........... 204/406

(Continued)

FOREIGN PATENT DOCUMENTS

CN   101163965 A   4/2008
DE   198 35 766 A1  2/2000

(Continued)

OTHER PUBLICATIONS

Briand, D., et al. : "Modulated Operating Temperature for MOSFET Gas Sensors: Hydrogen Recovery Time Reduction and Gas Discrimination," Sensors and Actuators B, Elsevier Sequoia S.A., Lausanne, CH, vol. 93, No. 1-3, pp. 276-285 (Aug. 1, 2003).

Kamata, M., et al. "Electromotive Force in a Nonisothermal and Connective System," Electrochimica Acta, Elsevier Science Publishers, Barking, GB, vol. 30, No. 5, pp. 521-525, (May 1, 1986).

(Continued)

*Primary Examiner* — Eugene Lee

(57) ABSTRACT

The invention relates to an electronic device for measuring and/or controlling a property of an analyte (100). The electronic device comprises: i) an electrode (Snsr) forming an interface with the analyte (100) in which the electrode (Snsr) is immersed in operational use, the interface having an interface temperature (T), and ii) a resistive heater (Htr) being thermally and capacitively coupled to the electrode (Snsr), the resistive heater (Htr) being configured for setting the interface temperature (T) by controlling a current through the resistive heater (Htr). The resistive heater (Htr) is provided with signal integrity protection for reducing the capacitive charging of the electrode (Snsr) by the resistive heater (Htr) if the current through the resistive heater (Htr) is modulated. The invention further relates to an electrochemical sensor for determining a charged particle concentration in the analyte (100) using the thermo-potentiometric principle, the electrochemical sensor comprising such electronic device. The invention also relates to an RFID tag and a semiconductor device comprising such electrochemical sensor. The effect of the feature of the invention is that the capacitive charging effect between the resistive heater and the electrode is reduced by the signal integrity protection.

13 Claims, 11 Drawing Sheets

(a)

(56) References Cited

U.S. PATENT DOCUMENTS

| | | | |
|---|---|---|---|
| 4,839,580 A * | 6/1989 | Moore et al. | 324/699 |
| 4,909,922 A * | 3/1990 | Kato et al. | 204/406 |
| 6,077,418 A * | 6/2000 | Iseri et al. | 205/775.5 |
| 6,411,110 B1 * | 6/2002 | Gilton | 324/718 |
| 7,011,735 B1 | 3/2006 | Neumann | |
| 7,462,512 B2 * | 12/2008 | Levon et al. | 438/123 |
| 7,754,065 B2 * | 7/2010 | Dieckmann et al. | 208/24 |
| 8,143,908 B2 * | 3/2012 | Uenluebayir et al. | 324/691 |
| 8,154,093 B2 * | 4/2012 | Bradley et al. | 257/414 |
| 2008/0257731 A1 | 10/2008 | Cramer et al. | |
| 2010/0112719 A1 * | 5/2010 | Doron et al. | 436/501 |

FOREIGN PATENT DOCUMENTS

| | | |
|---|---|---|
| GB | 2 088 565 A | 6/1982 |
| GB | 2 341 235 A | 8/2000 |
| WO | 01/32303 A1 | 5/2001 |
| WO | 2010/023610 A1 | 3/2010 |
| WO | 2010/023611 A1 | 3/2010 |

OTHER PUBLICATIONS

International Search Report for Int'l Patent Appln. No. PCT/IB2009/053148.

Klein, M. "Characterization of Ion-Sensitive Layer Systems with a $C(V)$ Measurement Method Operating at Constant Capacitance", Sensors and Actuators, B1, pp. 354-356 (1990).

Ylen, J.-P "Measuring, Modelling and Controlling the pH Value and the Dynamic Chemical State", Helsinki University of Technology Control Engineering Laboratory, 164 pgs, retrieved from the Internet at: lib.tkk.fi/Diss/2001/isbn9512257831/isbn9512257831.pdf (2001).

Bergveld, P. "Thirty Years of Isfetology: What Happened in the Past 30 Years and What May Happen in the next 30 Years", Sensors and Actuators B: Chemical, vol. 88, No. 1, 20 pgs (Jan. 1, 2003).

Yoshida, S. et al. "Development of a Wide Range pH Sensor based on Electrolyte-Insulator-Semiconductor Structure with Corrosion-Resistant $Al_2O_3$-$Ta_2O_5$ and $Al_2O_3$ $ZrO_2$ Double-Oxide Thin Films", Journal of the Electrochemical Society, 151 (3), 6 pgs (Jan. 22, 2004).

Jamasb, S. "An Analytical Technique for Counteracting Drift in Ion-Selective Field Effect Transistors (ISFETs)", IEEE Sensors Journal, vol. 4, No. 6, pp. 795-801 (Dec. 2004).

* cited by examiner (1) $\phi = (k^*T/(n^*q))^* \ln(a_1/a_2)$ $= (k^*T/(n^*q))^*(\ln a_1 - \ln a_2)$ $= \ln 10^*(k^*T/(n^*q))^*(\log a_1 - \log a_2)$ $= \ln 10^*(k^*T/(n^*q))^*(pa_2 - pa_1) \approx$ $= 2.3^*(k^*T/(n^*q))^*(pa2 - pa1)$ (2) $\Delta\phi = \phi_m - \phi_{ref}$ (3a) $\Delta\phi = 2.3^*k^*T/q^*(pHin - pHout) + (\phi_{cont} - \phi_{ref})$ (3b) $\Delta\phi = 2.3^*k^*T/q^*\alpha^*(pHpzc - pH) - \phi_{ref}$

Fig. 1

(4a) $\Delta\phi = 2.3*k*T/q*(pHin - pHout) + \phi_{cont} - \phi_{ref}$
$= m*T + \phi_{cont} - \phi_{ref}$ (4b) $m = 2.3*k/q*(pHin - pHout)$ (4c) ➡ $pHout = pHin - m*q/(k*2.3)$ (5a) $\Delta\phi = 2.3*k*T/q*\alpha*(pHpzc - pHout) - \phi_{ref}$
$= m*T - \phi_{ref}$ (5b) $m = 2.3*k/q*\alpha*(pHpzc - pHout)$ (5c) ➡ $pHout = pHpzc - m*q/(\alpha*k*2.3)$ (6) $\alpha = \dfrac{1}{\dfrac{2.3kC_s}{q^2\beta_s}T + 1}$ (7a) $\Delta\phi = 2.3*k*T_{fe}/q*\alpha_{fe}*(pHpzc_{fe} - pHout)$
$- 2.3*k*T_{se}/q*\alpha_{se}*(pHpzc_{se} - pHout)$ (7b) $\Delta\phi = 2.3*k/q*\alpha*(pHpzc - pHout)(T_{fe} - T_{se}) = m*\Delta T$

Fig. 3

REDUCING CAPACITIVE CHARGING IN ELECTRONIC DEVICES

FIELD OF THE INVENTION

The invention relates to an electronic device for measuring and/or controlling a property of an analyte. The invention further relates to an electrochemical sensor for determining a charged particle concentration in the analyte, the electrochemical sensor comprising such electronic device. The invention also relates to a semiconductor device and an RF-ID tag comprising such electrochemical sensor.

BACKGROUND OF THE INVENTION

There exist applications where a property of an analyte has to be measured or controlled. Generally, in operational use of such applications an electrode is immersed in the analyte for measuring and/or controlling (setting) a property of the analyte, such as a voltage (potential). The property to be measured or controlled often relates to an interface between the analyte and the electrode. The application may require that the temperature of the interface is precisely controlled or that the temperature can be varied. In some applications, such as applications implemented in integrated circuit technology, it is convenient to use a resistive heater to control or vary the temperature. In such applications the resistive heater needs to be put very close to the interface in order to be able to accurately control the interface temperature, i.e. to create a good thermal coupling between the resistive heater and the interface.

SUMMARY OF THE INVENTION

It is an object of the invention to provide an improved electronic device for measuring and/or controlling a property of an analyte.

The invention is defined by the independent claims. The dependent claims define advantageous embodiments.

In a first aspect, the invention relates to an electronic device for measuring and/or controlling a property of an analyte. The electronic device comprises:

an electrode forming an interface with the analyte in which the electrode is immersed in operational use, the interface having an interface temperature, and a resistive heater being thermally and capacitively coupled to the electrode, the resistive heater being configured for setting the interface temperature by controlling a current through the resistive heater, wherein the resistive heater is provided with signal integrity protection for reducing the capacitive charging of the electrode by the resistive heater if the current through the resistive heater is modulated.

The invention partially relies on the insight that the electrode-resistive heater configuration suffers from a drawback, namely the resistive heater may capacitively charge and/or discharge the electrode, which may result in undesired voltage pulses/peaks overloading a signal transducer (measurement amplifier) connected to the electrode in operation. This may deteriorate a measurement with the electrode or may induce noise on the property of the analyte, which has to be controlled by the electrode. The inventor has further discovered that it is very convenient to provide the resistive heater with signal integrity protection, instead of solving the problem at the side of the electrode (for example by means of signal enhancement circuitry).

In an embodiment of the electronic device in accordance with the invention the resistive heater comprises two terminals and a conductive path between the terminals, and the signal integrity protection comprises a driver circuit coupled to the terminals for controlling the current through the conductive path. The configuration of this embodiment opens up advantageous options.

In an embodiment of the electronic device in accordance with the invention the driver circuit is configured for applying voltage pulses to the two terminals of the resistive heater to obtain the current. The application of voltage pulse to a resistive heater is a convenient way of controlling the current. The (average) current level (and thereby the amount of heat generated) can be controlled by the pulse amplitude, pulse frequency and the pulse duty cycle.

In an embodiment of the electronic device in accordance with the invention the driver circuit is configured for applying the voltage pulses such that respective potentials of the two terminals are switched synchronously and oppositely with respect to each other. The advantage of this embodiment is that the capacitive charge induced by respective halves (from a respective terminal to a midpoint) of the heater on the electrode is opposite with respect to each other and thus cancels out. This is also referred to as "spatial averaging" in this description. At a mid-point of the resistive heater (halfway between the terminals) there is no capacitive charging effect in case of a fully symmetric electrode/heater design. Fully symmetric configurations provide for the best spatial averaging effect.

In an embodiment of the electronic device in accordance with the invention the respective potentials of the terminals are switched with equal amplitude. Optimal cancelling (spatial averaging) effect is achieved in this embodiment, where the amplitude of the voltage pulse on both terminals is the same (in particular when the electrode/heater design is symmetric).

In an embodiment of the electronic device in accordance with the invention the electrode has an electrode potential, and the driver circuit is configured for applying the voltage pulses such that a potential of one of said terminals, is switched symmetrically around a baseline reference potential while the other one of said terminals is connected to said baseline reference potential and at high-frequency to obtain an electrode signal with high-frequency-modulations. Furthermore, in this embodiment the signal integrity protection further comprises a low-pass filter connected to the electrode and being configured for filtering the high-frequency modulations in the electrode signal. In this embodiment the electrode signal is conveyed in the averaged measurement signal, wherein the averaging is done in the time-domain, i.e. time averaging, and is achieved by cancelling of the artifacts induced on the electrode by the resistive heater (the artifacts have opposite polarity). Preferably, the pulse frequency is adapted to the low-pass filter, i.e. that the frequency is higher than cut-off frequency of the filter.

In an embodiment of the electronic device in accordance with the invention the electrode and the resistive heater are arranged symmetrically with respect to each other to obtain equal impedances on both paths from each selective one of said terminals to a midpoint of the resistive heater. Fully symmetric configurations provide for the best spatial and time averaging effect.

In an embodiment of the electronic device in accordance with the invention the signal integrity protection further comprises a conductive shield arranged between the resistive heater and the electrode, wherein the conductive shield is connected to a fixed reference potential. In this embodiment the provision of the conductive shield reduces the capacitive coupling between the resistive heater and the electrode, which reduces the capacitive charging of the electrode. The resistive shield may also be provided such that it fully embeds the electrode in multiple dimensions, which reduces the capacitive coupling even further.

The pH-value is an integral parameter of every (aqueous) solution. It describes to which degree the solution is alkaline or acidic. Over a wide range it is well approximated by: $pH=-\log_{10}[H^+]$, wherein $[H^+]$ denotes the hydrogen ion concentration of the solution in mol/L. Measuring a pH-value of an aqueous solution is a routine task in the industry and also in laboratories for process control and analysis. However, it could also become interesting for a wider range of applications if the pH-measurement units (sensor plus electronics) become sufficiently inexpensive. For example, there is a large potential for pH-measurement to monitor the quality of (liquid) perishables in the supply chain or even at the customer's himself. Experimental techniques for measuring ion concentrations (in particular pH) can be divided into two classes, non-electrochemical methods, e.g. optical (indicator dyes), catalytic, and swelling of polymers (gels), and electrochemical methods. The latter are widely used for many applications in industry and laboratories. Electrochemical ion concentration sensors rely on the potentiometric principle, i.e. they measure the electrical potential $\phi$ at a solid/liquid interface or across a membrane which is a function of the ion concentration to be determined. $\phi$ can be calculated from the Nernst equation: $\phi=kT/(nq)\ln(a_1/a_2)$, wherein k is the Boltzmann constant, T the absolute temperature in Kelvin, q the elementary charge, n the ionic charge (e.g., n=1 for $H_3O^+$, $Na^+$; n=2 for $Ca^{2+}$), and $a_1$, $a_2$ the respective activities at both sides of the membrane/interface.

Ion concentrations at both sides of the membrane/interface are represented in terms of activities $a_i=f_i*c_i$ with $f_i$ being the respective activity coefficient ($f_i=1$ for diluted electrolytes) and $c_i$ the respective ion concentration. According to the Nernst equation the electrode potential is a logarithmic function of the ion activity on one side of the membrane/interface if the activity on the other side is kept constant. Depending on the type of ion described by "a", the sensor is sensitive to $H_3O^+$-ions, $Na^+$-ions, $Ca^{2+}$-ions, etc.

All major pH (ion) measurement electrodes operate according to the principle described above, including the well-known glass electrodes (different glass compositions have been developed that are sensitive to pH, pNa, pK, etc., respectively), antimony electrodes, ISFET's (Ion Sensitive Field Effect Transistors) and EIS capacitors (Electrolyte Insulator Semiconductor capacitors; here the flat-band voltage is a function of the pH/pNa/pK/etc of the electrolyte).

In order to measure the potential difference a reference electrode is needed; for the ISFETS and EIS devices the reference electrode defines the electrolyte potential to set the operating point and do the measurement. The potential of the reference electrode with respect to the electrolyte potential must remain constant irrespective of the electrolyte composition. Besides the standard hydrogen electrode the Ag/AgCl electrode is the most well-known reference electrode. It consists of a chlorinated silver wire in contact with a well defined electrolyte (often 3 mol/L KCl). Galvanic contact between the analyte and the electrolyte is established via a diaphragm, such as a porous frit from glass or ceramics. During operation the electrolyte must continuously flow out of the reference electrode into the analyte. Other reference electrodes, e.g. calomel (based on mercury) or Tl/TlCl electrodes, are used for specific applications, e.g. at elevated temperatures. Their principle is the same as for the Ag/AgCl electrode, in particular with respect to the use of liquid electrolyte and contact via a diaphragm.

The problem with most electrochemical sensors is that they require a reference electrode in order to determine the charged particle concentration from a measured potential (difference). Using reference electrodes, and in particular accurate reference electrodes, involves all kinds of difficulties such as the following:

Electrolyte outflow in a reference electrode through the diaphragm is essential. That means the electrolyte needs to be refilled regularly. Moreover, the pressure conditions must be such that the outflow is guaranteed, i.e. the pressure in the analyte cannot be higher than in the reference electrode (otherwise the analyte enters the reference electrode and changes its potential, which is called reference electrode poisoning;

Clogging of the diaphragm of the reference electrode causes measurement errors (depending on the application regular cleaning is needed);

Most reference electrodes have rather large dimensions, which makes it difficult/impossible to integrate them into a miniaturized device. Some miniature reference electrodes exist but they have a limited lifetime (because reference electrolyte cannot be refilled);

Reference electrodes have a limited temperature range, e.g., for high temperatures a Tl/TlCl electrode must be used; and Some reference electrodes may react to other environmental parameters, for example, the silver in Ag/AgCl electrodes is light sensitive.

Even pseudo-reference electrodes suffer from several disadvantages, such as:

complex (expensive) integration, corrosion, interface leakage, food and bio-compatibility issues.

Electrochemical sensors that use the thermo-potentiometric principle do not suffer from the above drawbacks, because they do not need a conventional reference electrode. Some embodiments only need a pseudo-reference electrode and others do not need a reference electrode at all.

The principle behind electrochemical sensor using the thermo-potentiometric principle can be understood as follows. In electrochemical sensors, the reactions of interest occur at the surface of the measurement electrode. It is of interest to control or measure the potential drop across the interface between the surface of the measurement electrode and the solution (i.e., the surface potential). However, it is impossible to control or measure this surface potential without placing another electrode in the solution. Thus, two potentials must be considered, neither of which can be measured independently. The reason why in the electrochemical sensors known from the prior art the reference electrode must produce a fairly accurate reference voltage is that otherwise the charged particle concentration cannot be determined from the Nernst equation, i.e. the absolute value of the surface-potential must be known.

An inventive thought is that the charged particle concentration may also be determined in a different manner, namely it may be determined from the surface-potential versus temperature curve, and in particular from the slope of this curve.

In a second aspect, the invention relates to an electrochemical sensor for determining a charged particle concentration in the analyte using the thermo-potentiometric principle, the electrochemical sensor comprising the electronic device. The invention is particularly advantageous in electrochemical sensors of this kind. The two embodiments discussed hereinafter elaborate on the thermo-potentiometric principle.

In an embodiment of the electrochemical sensor in accordance with the invention the electrode is a sensor electrode for measuring a surface-potential at the interface, and the electrochemical sensor further comprises a control means for measuring the surface-potential at at least two different temperatures of the interface to obtain at least two measurement points of a surface-potential versus interface-temperature curve. Furthermore, in this embodiment the resistive heater is arranged for setting the interface temperature at the at least two different values.

In this embodiment, the earlier-mentioned thermo-potentiometric principle is implemented as follows. The electrochemical sensor comprises a sensor electrode for measuring a surface-potential at an interface of the sensor electrode and the analyte in which the sensor electrode is immersed in operational use. The electrochemical sensor further comprises a control means for measuring the surface-potential at at least two different temperatures of the interface between the sensor electrode and the analyte to obtain at least two measurement points of a surface-potential versus interface-temperature curve. The electrochemical sensor further comprises a resistive heater which is arranged for setting the interface temperature at the at least two different values.

The electrochemical sensor enables determination of the charged particle concentration in the analyte as follows. First, the control means ensures that the temperature of the interface between the sensor electrode and the analyte reaches a first value. Subsequently, the sensor electrode can be "read-out" to give the surface-potential corresponding with the first temperature. These two steps are subsequently repeated for at least one other temperature different from the first temperature, which gives a total of at least two measurement points of a surface-potential versus temperature curve and which enables to determine a corresponding slope. The absolute values of the corresponding potential of the at least two measurement points in said curve are dependent on the absolute potential of the analyte as defined by the reference electrode. However, it is not required that the reference interface-potential is known and accurately determined, i.e. that it does not vary with the charged particle concentration, because the charged particle concentration is determined by the slope of said curve. Once the slope has been determined, the corresponding charged-particle concentration can be calculated from the slope. For this purpose a pseudo-reference electrode is sufficient. A pseudo-reference electrode is so named because it does not maintain a constant potential (potential depends on analyte composition); therefore, by definition, it is not a true/real reference electrode. However, its potential depends on conditions in a well-defined manner; if the conditions are known, the potential can be calculated and the electrode can be used as for reference potential.

In an embodiment of the electrochemical sensor in accordance with the invention the sensor further comprises a pseudo-reference electrode for providing a reference potential to the analyte, the reference potential being defined at a further interface of the pseudo-reference electrode and the analyte in which the pseudo-reference electrode is immersed in operational use. As the sensor in accordance with the invention only needs a pseudo-reference electrode, this reference electrode may be advantageously integrated with the measurement electrode.

In an embodiment of the electrochemical sensor in accordance with the invention the electrode is a sensor electrode comprising: i) a first electrode with a first ion-sensitive dielectric provided thereon, the first electrode being arranged for contacting the analyte via the first ion-sensitive dielectric to obtain a first interface between the first ion-sensitive dielectric and the analyte, and ii) a second electrode with a second ion-sensitive dielectric provided thereon, the second electrode being arranged for contacting the analyte via the second ion-sensitive dielectric to obtain a second interface between the second ion-sensitive dielectric and the analyte. Furthermore, in this embodiment the electrochemical sensor further comprises a control means for measuring a potential difference between the first electrode and the second electrode at at least two different values of a temperature difference between the first interface and the second interface to obtain at least two measurement points of a surface-potential versus interface-temperature curve. Moreover, the resistive heater is arranged for setting the temperature difference at the at least two different values.

In this embodiment, the earlier-mentioned thermo-potentiometric principle is implemented as follows. The electrochemical sensor comprises a sensor electrode comprising: a first electrode with a first ion-sensitive dielectric provided thereon. The first electrode is arranged for contacting the analyte via the first ion-sensitive dielectric to obtain a first interface between the first ion-sensitive dielectric and the analyte. The sensor electrode further comprises a second electrode with a second ion-sensitive dielectric provided thereon. The second electrode is arranged for contacting the analyte via the second ion-sensitive dielectric to obtain a second interface between the second ion-sensitive dielectric and the analyte. The electrochemical sensor further comprises a control means for measuring a potential difference between the first electrode and the second electrode at at least two different values of a temperature difference between the first interface and the second interface to obtain at least two measurement points of a surface-potential versus interface-temperature curve. The resistive heater is arranged for setting the temperature difference at the at least two different values.

The electrochemical sensor enables determination of the charged particle concentration in the analyte as follows. First, the control means/resistive heater ensure that the temperature difference of the interface between the first electrode and the analyte reaches a first value. Subsequently, the first electrode and the second electrode can be "read-out" to give the potential difference corresponding with the first temperature difference. These two steps are subsequently repeated for at least a second temperature difference, wherein the second temperature difference differs from the first temperature difference. This gives a total of at least two measurement points of a surface-potential versus temperature curve and which enables to determine a corresponding slope. Once the slope has been determined, the corresponding charged-particle concentration can be calculated from the slope.

The absolute values of the corresponding potential of the at least two measurement points in said curve are dependent on the absolute potential of the analyte as defined by a reference electrode. However, in the electrochemical sensor of this embodiment it is not required that the reference potential is known or accurately determined, nor that it does not vary with the charged particle concentration, because the charged particle concentration is determined by the slope of said curve. Moreover, in the electrochemical sensor of this embodiment it is even not required to set a DC-potential of the analyte with the reference electrode. In the prior art solutions, the setting of the DC-potential of the analyte with the reference electrode closes the measurement "loop" and thereby defines the DC-potential difference between the reference electrode and the measurement electrode. In the electrochemical sensor of this embodiment it is sufficient to close the measurement signal-path using a capacitor. In operational use this signal path comprises:

a first capacitance defined by the first electrode, the first ion-sensitive dielectric, and the analyte;

a second capacitance defined by the second electrode, the second ion-sensitive dielectric, and the analyte;

a resistance defined by the analyte between the respective ion-sensitive dielectrics of the first and second electrode, and an input impedance of a voltage- or current-measurement device connected between the first electrode and the second electrode for measuring the potential difference.

In this embodiment the signal-path is closed with a second electrode with a second first-ion-sensitive dielectric which forms a capacitance together with the analyte. This is sufficient here, because the potential difference is modified by the temperature and thus generates a transient voltage. For measurement of transient voltages there is no need to establish a closed DC-loop. A reference electrode (with or without reference electrolyte) to set a DC-potential of the analyte, is no longer required.

In an embodiment of the electrochemical sensor in accordance with the invention the control means comprises a controller, the controller being coupled to the sensor electrode and being arranged for initiating the measuring of the surface-potential with the sensor electrode at the at least two different values.

In a third aspect, the invention relates to a semiconductor device comprising the electrochemical sensor in accordance with the invention. It is a great advantage of the invention that the electrochemical sensor can be integrated into a semiconductor device. All mentioned features in the embodiments can be integrated onto the same semiconductor device, including the resistive heater, the control means, the controller, the pseudo-reference electrode, etc.

In a fourth aspect, the invention relates to an RF-ID tag comprising the electrochemical sensor in accordance with the invention. The invention is advantageously applied in this application area.

These and other aspects of the invention are apparent from and will be elucidated with reference to the embodiments described hereinafter.

BRIEF DESCRIPTION OF THE DRAWINGS

In the drawings:

FIG. 1 shows some formula's for explaining the potentiometric measurement principle as known from the prior art;

FIG. 3 shows some formulas for explaining the thermo-potentiometric measurement principle, which may benefit from the invention;

DETAILED DESCRIPTION OF THE PREFERRED EMBODIMENT

Figure 2:
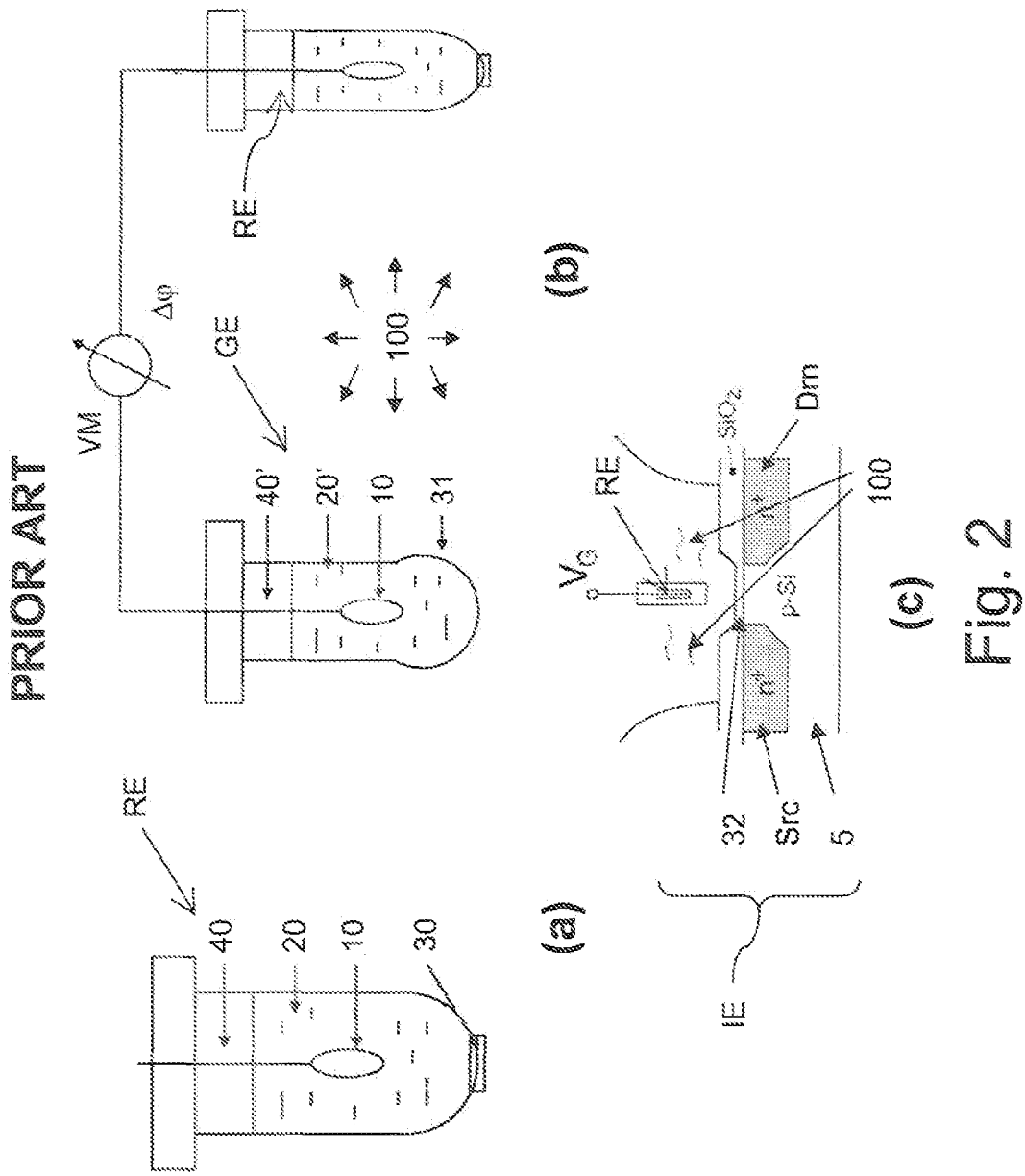
FIGS. 2(a) to 2(c) show conventional electrodes and reference electrodes known from the prior art.

The invention aims at providing an electronic device for measuring and/or controlling a property of an analyte by means of an electrode, wherein a resistive heater is used for setting a temperature of an interface between the electrode and the analyte. The invention further aims at providing an electrochemical sensor for determining a charged particle concentration, wherein the electrochemical sensor comprises such electronic device, and to a semiconductor device and an RFID tag comprising such electrochemical sensor. The invention is advantageously applied to electrochemical sensors relying on the thermo-potentiometric principle, i.e. electrochemical sensors that determine the charged particle concentration from a surface-potential versus interface-temperature (or temperature difference) curve, wherein the temperature is set and modulated by means of a resistive heater. The invention aims at reducing capacitive charging effects between the resistive heater and the interface (electrode) to which it is thermally, but also capacitively, coupled. To achieve this signal integrity protection has been added to the resistive heater.

In order to facilitate the discussion of the detailed embodiments a few expressions are defined hereinafter.

Throughout this description the term "interface temperature" should be interpreted as the temperature of a volume around the interface which includes a sub-volume with electrode material and a sub-volume with analyte.

In electrochemistry, the Nernst equation is an equation which can be used (in conjunction with other information) to determine the equilibrium reduction potential of a half-cell in an electrochemical cell.

A half cell is a structure that contains a conductive electrode and a surrounding conductive electrolyte separated by a naturally-occurring Helmholtz double layer. Chemical reactions within this layer momentarily pump electric charges between the electrode and the electrolyte, resulting in a potential difference between the electrode and the electrolyte. The typical reaction involves a metal atom in the electrode being dissolved and transported as a positive ion across the double layer, causing the electrolyte to acquire a net positive charge while the electrode acquires a net negative charge. The growing potential difference creates an intense electric field within the double layer, and the potential rises in value until the field halts the net charge-pumping reactions. In a similar way the Nernst equation also describes the surface potential at the interface of a dielectric and an electrolyte or across a membrane with different ion concentrations in the electrolytes on either side.

Throughout this description the term "reference electrode" refers to an electrode which has a stable and well-known electrode potential. The high stability of the electrode potential is usually reached by employing a redox system with constant (buffered or saturated) concentrations of each participants of the redox reaction. Reference electrodes are used to build an electrochemical cell in conjunction with an electrode the potential of which is to be determined. Each electrode represents a half cell; both are required to complete the circuit and measure the unknown potential.

Throughout this description the term "pseudo-reference electrode" refers to a reference electrode which does not maintain a constant potential. By definition, a pseudo-reference electrode is not a true reference electrode. However, its potential depends on conditions in a well-defined manner; if the conditions are known, the potential can be calculated and the electrode can be used as for reference potential.

Throughout this description the term "measurement electrode" is considered either a glass electrode, gate of an ISFET, electrode of an EGFET, EIS capacitor or a metal electrode connected to a measurement amplifier.

Throughout this description the term "charged particle" refers to ions and charged bio-molecules.

Throughout this description the term "interconnect layer" should be considered as synonym to "metallization layer" or "metal layer". Both terms are used interchangeably and have to be interpreted as the layer comprising conductors (any conducting material), the insulating layer in which the conductors are embedded, and any vias (=contacts) to underlying layers. These terms are well-known to the person skilled in the art of semiconductor technology.

Throughout this description the term "substrate" should be interpreted broadly. The substrate may comprise an active layer with elements, such as transistors and diodes, which form the components of an electronic circuit. The substrate may further comprise interconnections between the elements which may be laid out in one or more interconnect layers and may further contain passive elements such as capacitors, resistors and inductors. In the figures, the elements have been left out in order to facilitate the understanding of the invention. The active layer in which the elements are formed may also be called a semiconductor body. The semiconductor body may comprise any one of the following semiconductor materials and compositions like silicon (Si), germanium (Ge), silicon germanium (SiGe), gallium-arsenide (GaAs) and other III-V compounds like indium-phosphide (InP), cadmium sulfide (CdS) and other II-VI compounds, or combinations of these materials and compositions as well as semiconducting polymers. The active elements together may form an electronic circuit. In any case, connection of the active elements is done via interconnect layers. These interconnect layers have parasitic capacitances which are defined by the dielectric constant of surrounding materials. The semiconductor body may even comprise contacts to lower layers (e.g. diffusion regions at the surface of an active region).

The description of the figures deals for a large part with the application of the invention in electrochemical sensors relying on the thermo-potentiometric principle. It must be noted, however, that the invention is applicable in a broader field, namely in any electronic device for measuring and/or controlling a property of an analyte, which comprises an electrode to be immersed in the analyte and which forms an interface with the analyte in operational use, wherein the interface-temperature is set by means of a resistive heater which is thermally and capacitively coupled to the electrode.

FIG. 1 shows some formula's for explaining the potentiometric measurement principle as known from the prior art. In the description of the figures the main principle will be explained with measurement of a concentration of hydrogen ions (pH-value). However, it must be stressed that the invention is also applicable to any other kind of charged particle concentration, i.e., $Na^+$-ions, $K^+$-ions, $Ca^{2+}$-ions, etc.

The pH-value is an integral parameter of every (aqueous) solution. It describes to which degree the solution is alkaline or acidic. Over a wide range it is well approximated by: $pH = -\log_{10}[H^+]$, wherein $[H^+]$ denotes the proton concentration of the solution in mol/L. pH-measurement is a routine task in industry and also in laboratories for process control and analysis. However, it could also become interesting for a wider application range if the pH-measurement units (sensor plus electronics) become sufficiently inexpensive. E.g., there is a large potential for pH-measurement to monitor the quality of (liquid) perishables in the supply chain or even at the customer himself. Experimental techniques for measuring ion concentrations (as is the case in pH-measurements) can be divided into two classes, non-electrochemical methods, e.g., optical (indicator dyes), catalytic, and swelling of polymers (gels), and electrochemical methods. The latter are widely used for many applications in industry and laboratories. Electrochemical ion concentration sensors rely on the potentiometric principle, i.e. they measure the electrical potential $\phi$ across a solid/liquid interface which is a function of the ion concentration to be determined. The potential $\phi$ can be calculated from the Nernst equation, given in formula (1) of FIG. 1. In this formula k is the Boltzmann constant, T the absolute temperature in Kelvin, q the elementary charge, and n the ionic charge (e.g. n=1 for $H_3O^+$, $Na^+$; n=2 for $Ca^{2+}$). Ion concentrations at both sides of the membrane/interface (1 and 2) are represented in terms of activities $a_i = f_i * c_i$ with $f_i$ being the activity coefficient ($f_i=1$ for diluted electrolytes) and $c_i$ the respective ion concentration in mol/L. According to the Nernst equation the electrode potential is a logarithmic function of the ion activity on one side of the membrane/interface if the activity on the other side is kept constant. Depending on the type of ion described by parameter "a" the sensor is sensitive to $H_3O^+$-ions, $Na^+$-ions, $Ca^{2+}$-ions, etc.

FIGS. 2(a) to 2(c) show conventional electrodes and reference electrodes known from the prior art. All major pH-(ion)-measurement electrodes work according to the principle described above, including the well-known glass electrodes (different glass compositions sensitive to pH, pNa, pK etc. have been developed), antimony electrodes, ISFET's (Ion Sensitive Filed Effect Transistor) and EIS capacitors (Electrolyte Insulator Semiconductor capacitor; here the flat-band voltage is a function of the pH of the electrolyte). It is not possible to measure a potential, but it is possible to measure potential differences, i.e. voltages. In any case, in order to measure a potential difference with a measurement electrode a reference electrode is needed, wherein the potential difference is generated by a difference in the measurement electrode potential $\phi_m$ and the reference electrode potential $\phi_{ref}$ (see formula (2) in FIG. 1). In the case of ISFET and EIS devices as measurement electrode the reference electrode is also used to set the operating point and close the electric loop. In the conventional potentiometric measurements of the prior art, the potential of the reference electrode $\phi_{ref}$ with respect to the electrolyte potential must remain constant irrespective of the analyte composition. Thus, in the conventional potentiometric measurements of prior art, what is measured is the potential difference $\Delta\phi$ between the measurement electrode potential $\phi_m$ and the reference electrode potential $\phi_{ref}$. This is given by formula (2) in FIG. 1.

In the case of a pH-measurement with a glass-electrode and a conventional reference electrode (with a reference liquid), the potential difference can be given by (3a) formula in FIG. 1. In formula (3a) pHin stands for the pH of the electrolyte in the glass-electrode and pHout stands for the pH of the analyte (which has to be determined). In fact formula (3) is the sum of two surface potentials at the inside and outside of the glass electrode as well as the contact potential of the wire inside the glass electrode with the electrolyte in the glass-electrode $\phi_{cont}$ and the reference electrode potential $\phi_{ref}$. However, in this configuration these terms cancel each other out when both electrodes have the same temperature, material and same reference electrolyte. The derivation of formula (3a) and more information on reference electrodes can be found in the following publication:

"*Measuring, modeling, and controlling the PH-value and the dynamic chemical state*." By Jean-Peter Ylén, Helsinki University of Technology, Control Engineering Laboratory, Report 127, Espoo 2001 [REF1]. This document has been incorporated by reference in its entirety.

In the case of a pH-measurement with an ISFET-measurement electrode and a conventional reference electrode, the potential difference can be given by (3b) formula in FIG. 1. In formula (3b) parameter "pHpzc" stands for the point of zero charge of the ISFET-measurement electrode (a material property defined by the dielectric sensor layer of the ISFET) and pHout stands for the pH of the analyte (which has to be determined). The derivation of formula (3b) and more information on ISFET electrodes can be found in the following publication:

P. Bergveld, "*Thirty years of ISFETOLOGY. What happened in the past 30 years and what may happen in the next 30 years.*", Sensors and Actuators B 88 (2003) 1-20 [REF2]. This document has been incorporated by reference in its entirety.

Besides the standard hydrogen electrode, the Ag/AgCl electrode is the most well-known reference electrode. This reference electrode RE is illustrated in FIG. 2(*a*). It consists of a chlorinated silver wire 10 (Ag/AgCl) in contact with a well-defined electrolyte 20 (often 3 mol/L KCl). Galvanic contact to the analyte is established via a diaphragm 30 (porous frit from glass or ceramics, etc.). During operation the electrolyte 20 must continuously flow out of the reference electrode RE into the analyte. Other reference electrodes, e.g. calomel electrodes (based on mercury) or Tl/TlCl electrodes are used for specific applications, e.g. at elevated temperatures. Their principle is the same as for the Ag/AgCl electrode, in particular the use of a liquid electrolyte 20 and contact via a diaphragm 30. The chlorinated silver wire 10 is connected to a contact cable 40.

FIG. 2(*b*) illustrates a measurement set-up in which the reference electrode RE is used in combination with a glass electrode GE. Both electrodes GE, RE are immersed into the analyte 100 in operational use. The glass electrode GE comprises a chlorinated silver wire 10 (Ag/AgCl) in contact with an electrolyte 20' (buffer solution) with a well-defined $pH_{in}$-value. The electrolyte 20' is provided in a pH-sensitive glass membrane 31, which is produced from a special glass. Its thickness is usually between 50-200 μm, but in the measurement of very aggressive solutions it can be even 1 mm. After immersion in water the glass electrode can measure the process solution 100 (analyte). A potential difference between the analyte 100 and the glass surface is created, and this difference is a function of the activity of $H_3O^+$-ions and thus also a function of the pH-value of the analyte 100. The chlorinated silver wire 10' is connected to a further contact cable 40'. The cable 40 and the further cable 40' are both connect to the input of a voltmeter VM. The voltmeter gives the potential difference Δϕ as given by formula (3a) in FIG. 1. More information about glass electrodes can be found in the first reference (REF1) given in this description.

FIG. 2(*c*) illustrates a measurement set-up in which the reference electrode RE is used in combination with an ISFET measurement electrode IE. Both electrodes IE, RE are immersed into the analyte in operational use. The ISFET measurement electrode IE comprises a transistor structure, which is very similar to a conventional field-effect transistor (FET). It comprises a p-type substrate 5 having an n-type source Src and an n-type drain Drn provided at a surface thereof defining a channel region in between. A gate dielectric 32 is provided on the substrate 5 covering source Src, drain Drn and channel. Alternative a p-type transistor can be used. A main difference with respect to a conventional MOSFET is that the gate dielectric 32 is in direct contact with the analyte 100 instead of with a poly/metal gate contact. The gate dielectric 32 is the ion/pH sensitive layer (in an example embodiment it comprises $SiO_2$, but other dielectrics, such as $Ta_2O_5$ can also be used). The transistor acts as transducer that converts the potential difference into a current between the source Src and drain Drn of the transistor. Above the channel region the dielectric may be thinner than elsewhere, in order to increase the sensitivity of the ISFET (better control of the channel in case of a predefined surface potential generation at the dielectric layer 32). More information about ISFET's can be found in the second reference (REF2) given in this description. A reference electrode RE is provided in the analyte 100 in order to establish a "working point" (reference potential) for the ISFET and define the analyte potential. A potential set by this reference electrode RE may be considered as the gate voltage $V_G$ of a conventional field-effect transistor. In the prior art pH-measurements it is of utmost importance that the potential of the reference electrode is independent of the composition of the analyte.

FIG. 3 shows some formulas for explaining the thermo-potentiometric measurement principle, which may benefit from the invention. An essential feature of the thermo-potentiometric measurement is to execute potentiometric pH/ion measurements at different temperatures in the (same) analyte. While temperature changes must be compensated or taken into account with the conventional potentiometric measurement principle of the prior art the invention exploits the temperature dependency of the sensor output to determine the quantity to be measured, e.g., the pH-value or ion concentration of a solution. The arguments described hereafter relate to pH-value but also apply to ion concentration or charged biomolecule concentration, then the pH needs to be replaced by pK and the charge number n must be taken into account).

The potential difference equation for a combination of a glass electrode and a conventional reference electrode (with reference liquid) is repeated in formula (4a) in FIG. 3, wherein pHout denotes the pH-value at the outside (analyte) and pHin denotes the pH-value of the electrolyte inside (ln 10≈2.3). It must be realized that formula (4a) can be looked at differently. According to this formula Δϕ shows a linear dependence on T with the slope of the straight line m given by formula (4b) in FIG. 3. It must be noted that all parameters of this formula are known or fixed, except for pHout which is the pH-value of the analyte to be measured. Following this approach the pH-value of an analyte can be obtained by recording the potential difference Δϕ at different temperatures (or temperature differences in case of two measurement electrodes), determining the slope m of the Δϕ-T curve and subsequently calculating the pH-value using formula (4c) in FIG. 3. Alternatively, it is also possible to determine the slope by varying the temperature of two electrode-analyte interfaces in a different way in order to create said temperature differences (instead of only setting a temperature of the first interface). The surface potential difference Δϕ can then be determined by determining the potential difference between said two electrodes.

Figure 4:
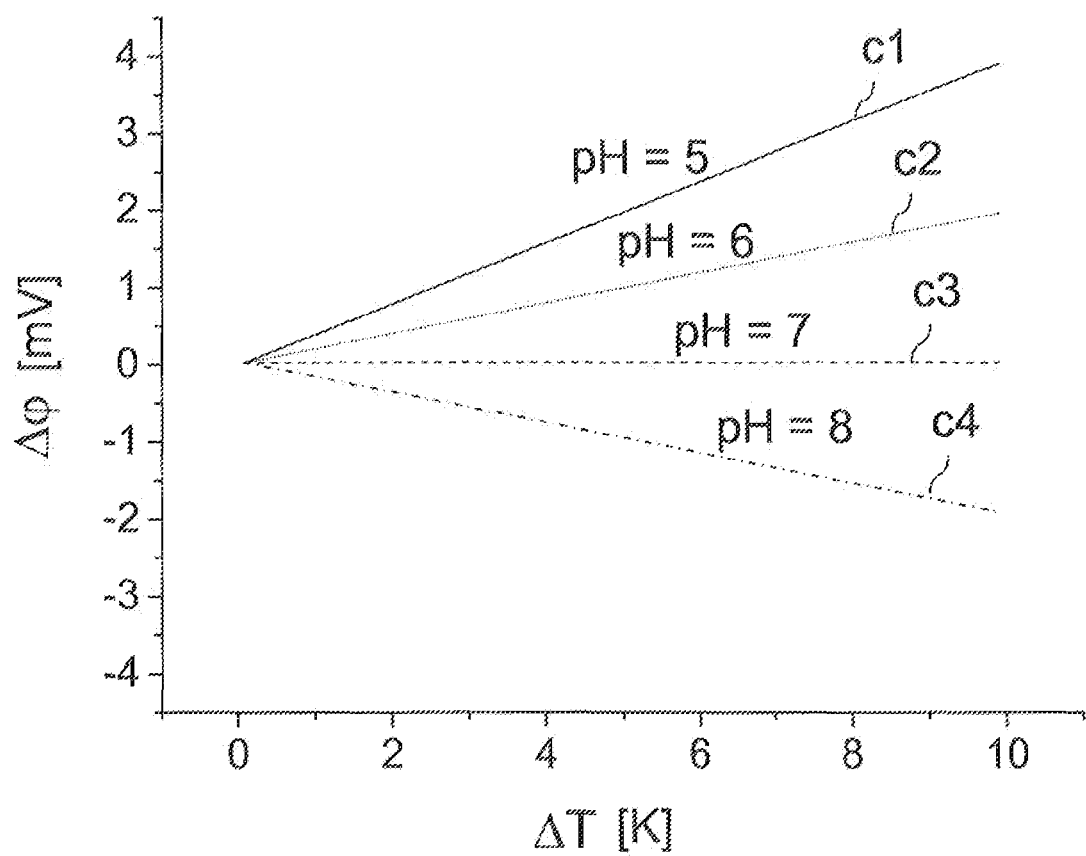
FIG. 4 shows a diagram with a couple of potential difference versus interface-temperature change curves for different charged particle concentrations in an analyte.

FIG. 4 shows a diagram with a couple of potential difference versus interface-temperature change curves for different charged particle concentrations in an analyte. The diagram shows Δϕ-ΔT-curves for various pHout-values in a temperature range 0K-10K (pHin=7). These curves have a direct relation with the surface-potential versus interface-temperature curves. The slopes of the curves allow a clear discrimination of the different pH-values. Four curves c1, c2, c3, c4 illustrate a pH-value equal to 5, 6, 7, and 8, respectively. Which curve runs horizontal depends on the value of parameter "pHin". In principle parameter "pHout" can be calculated without calibrating the sensor since all parameters in formula (4a) in FIG. 3 are known. In reality calibration may still be advisory because of components of the system that do not behave ideally and may be (slightly) temperature dependent.

Since the information about the pH-value (hydrogen-ion concentration) is conveyed in the slope of the $\Delta\phi$-$\Delta T$-curves rather than in the absolute value of $\phi$ (as is the case with conventional potentiometric measurements) any vertical shift of the curves has no effect on the measurement. Thus any potential offset caused by using a non-accurate reference electrode or a pseudo-reference electrode does not influence the measurement. A pseudo-reference electrode consists of a simple metal wire (e.g. Pt or Ag/AgCl) immersed in the analyte (sample solution). A pseudo-reference electrode provides a constant reference potential, but this is usually unknown since it depends on the analyte composition (e.g. its ion concentration).

In the electrochemical sensor using the thermo-potentiometric principle no reference electrode is required at all. Even a pseudo reference electrode is no longer required in some embodiments. Instead, a first electrode and the second (similar) electrode may be used, which together with the analyte and a measurement device close the electrical circuit and the respective (transient) temperatures of the respective electrode-analyte interfaces, cause a (transient) potential difference between the electrodes. For a precise measurement at a specific temperature it must only be made sure that the potential of the respective electrodes and analyte remains constant during the measurement itself, i.e. during recording of the respective $\phi$-values.

For the method it is not even necessary to know the absolute temperature of said interfaces. The only value which must be known (in arbitrary units) is the change in the temperature difference between said interfaces over the different measurements. For example, in a situation where only the first interface is heated, the temperature T for the first interface can be given as: $T=T_0+a*U_2/R$, wherein parameter "$T_0$" denotes the start temperature, parameter "R" denotes the ohmic resistance of a resistive heater, parameter "U" denotes the applied voltage. Parameter "a" comprises all other system parameters such as geometric factors, heat conductance etc. Substituting this formula for the temperature with formula (4a) in FIG. 3, gives a formula for the potential difference $\Delta\phi$ as a function of voltage "U" (and thus heat power). The absolute value of the start temperature $T_0$ does not need to be known, since it only causes a vertical shift of the curve, whereas the pH-value (pHout) is conveyed in the slope. A calibration of the system (i.e. measure the slope of a curve with a buffer of defined pHout) may be necessary in order to determine parameter "a". Moreover, parameter "a" should preferably remain constant between calibration and real measurement since it directly affects the slope. Also, it must be noted that the temperature difference between the first interface and the second interface follows directly from the temperature formula as the second interface is not heated in this example (no temperature change).

Experiments have indicated that thermal conduction plays a major role, i.e. the temperature is governed by the heating power (equilibrium is almost reached instantly) after switching the heater on. A temperature T that is proportional to supplied energy may be correct if the system is thermally closed without heat loss.

Potentiometric measurements as known from the prior art are static measurements, which rely on the thermodynamic equilibrium. Static measurements are often subject to drift, which makes frequent calibration necessary. Besides the associated effort and cost, some systems are difficult to calibrate, e.g. because the sensor is fixed in a vessel/pipe and would need to be removed or because the system cannot be accessed at all (perishable monitoring, medical applications). Drift is a particular problem for ISFET sensors. Various algorithms and procedures have been developed to predict drift and correct the measurements (see [REF2]) Moreover, new sensors must equilibrate for a certain time before they can be used. An advantage of the measurement principle of the invention is that due to the dynamic measurement principle drift is considerably reduced with our invention increasing the calibration intervals and measurement accuracy. More information on drift and counter-measures can be found in the following publication:

S. Jamsab, *"An Analytical Technique for Counteracting drift in Ion-Selective Field effect Transistors (ISFETs)"*, IEEE Sensors J., 4 (6), 795-801, 2004 [REF3]. This document has been incorporated by reference in its entirety.

Another advantage of the thermo-potentiometric measurement principle is the noise reduction. If the slope of a $\Delta\phi$-$\Delta T$-curve is determined by fitting a straight line to several $\phi$ values recorded at different temperatures, noise and statistical measurement errors are averaged out.

Until now, for the sake of clarity only the fundamental principles and equations have been shown and discussed. In real applications it might be slightly more complex. This also depends on the type of measurement electrode and reference electrodes chosen.

In the case of a pH-measurement with an ISFET-measurement electrode and a reference electrode, the potential difference can be given by formula (5a) in FIG. 3 wherein the first part describes the surface potential (which yields the information on the pH-value of the analyte) of the dielectric/analyte interface, wherein parameter pHpzc denotes the point-of-zero-charge, i.e. the pH-value of the analyte for which the oxide surface is electrically neutral, wherein parameter pHout denotes the actual pH-value of the analyte in contact with the dielectric, wherein parameter "$\alpha$" denotes a temperature dependent sensitivity parameter which is characteristic for the specific ISFET sensor dielectric. Parameter "$\alpha$" lies between 0 and 1 (in case of a sensitivity equal to 1 the sensor has the maximum sensitivity). Formula's (5b) and (5c) can be derived from formula (5a) in a way that is similar to that of formula's (4b) and (4c) in FIG. 3.

Parameter "$\alpha$" for an ISFET is known to be defined as given in formula (6) in FIG. 3, wherein parameter $C_S$ denotes the double layer capacitance (which depends on the ion concentration in the analyte), and wherein parameter $\beta_S$ denotes the surface buffer capacity which is a material parameter of the sensor dielectric. Other parameters are already explained earlier in the description.

The temperature dependency of the sensor sensitivity $\alpha$ may complicate the measurement method a bit. It can be addressed in several ways (or combinations thereof).
1) Use a sensor dielectric material with high surface buffer capacity $\beta_S$. This measure minimizes the temperature dependence of the sensitivity $\alpha$. The advantage of this approach is that the measurement principle described above can applied without modification. In a preferred embodiment the sensor dielectric material comprises tantalum oxide ($Ta_2O_5$) which has the advantage that it has a very high $\beta_S$.
2) Perform the different temperature measurements in a small temperature "window", e.g. 5K. Within this temperature window the sensitivity $\alpha$ may be assumed to be constant. Consequently, a small change in the sensitivity $\alpha$ results in a relatively small error and can be neglected. This second approach requires that the calibration and "real" measurement to be made are done at the same temperature. Otherwise the error will increase because of the earlier mentioned temperature dependency, which thus results in different slopes.

3) Determine $C_S$ and $\beta_S$ during sensor calibration. A single calibration run with one reference solution is sufficient. However, the surface potential $\phi$ must be measured for several temperatures to provide enough data points for fitting the $\Delta\phi$-T-curve in order to determine $C_S$ and $\beta_S$. This is a very accurate approach but the absolute temperature must be known. A temperature sensor for determining the absolute temperature is thus required.

It is possible to do a pH-measurement with two measurement electrodes. In such measurement set-up the potential difference can be given by formula (7a) in FIG. 3 wherein the first part describes the surface potential (which yields the information on the pH-value of the analyte) of the first dielectric/analyte interface, wherein parameter $pHpzc_{fe}$ denotes the point-of-zero-charge of the first electrode. Parameter $T_{fe}$ denotes the temperature of the first interface. Parameter pHout denotes the actual pH-value of the analyte in contact with the first dielectric. Parameter "$\alpha_{fe}$" denotes a temperature dependent sensitivity parameter of the first measurement electrode which is characteristic for the specific sensor dielectric. The second part of formula (7a) describes the surface potential (which yields the information on the pH-value of the analyte) of the second dielectric/analyte interface, wherein parameter $pHpzc_{se}$ denotes the point-of-zero-charge of the second electrode. Parameter $T_{se}$ denotes the temperature of the second interface. Like for the first part of the formula, parameter pHout denotes the actual pH-value of the analyte in contact with the second dielectric. Parameter "$\alpha_{se}$" denotes a temperature dependent sensitivity parameter of the second measurement electrode which is characteristic for the specific sensor dielectric. When the parameters of the first electrode and the second electrode are identical (which is automatically the case if they are of the same kind and have the same structure, materials, and dimensions) formula (7a) can be rewritten into formula (7b), which clearly illustrates the linear dependency of the potential difference $\Delta\phi$ on the temperature difference $\Delta T$.

The method for measuring pH or ion concentrations can be realized in different ways. In any case a first and a second electrode are required. In operational use, the first electrode forms a first interface with the analyte and the second electrode forms a second interface with the analyte. At least one of the electrodes must be provided with a small heater/cooler. This heater configuration enables to create a (variable) temperature difference between respective interfaces with the analyte. The heater/cooler heats/cools the analyte in close proximity to the first interface. The sensor readings (representing $\phi$) at different temperature differences (the temperature (difference) may be measured with an integrated sensor or determined from heating power) are stored or plotted. This provides measurement points of a surface-potential versus temperature curve. Subsequently, the charged particle concentration may be obtained from the slope of said curve according to the method described above. Instead of a close-by heater/cooler the analyte temperature can also be controlled by a remote device and applied to the sensor by a fluidic system (e.g. flush liquid onto sensor).

If no temperature sensor is used in the method, sufficient time must pass between subsequent heat pulses to allow cooling of the sensor to the initial (ambient) temperature. If only short heat pulses are used a heat wave will propagate towards the dielectric/analyte interface leading to a transient temperature increase. Continuous measurement of the potential difference (transducer output) will result in a maximum value, which value shall be used for further data extraction (when this value is reached the temperature at the interface is highest before it cools off again). To increase measurement accuracy a curve can be fitted to determine the extreme value (taking into account the temporal behavior of the temperature at the interface following a heat pulse). A simpler way is to average a few values in an interval around the extreme value.

Where in this specification the wording "obtaining of measurement points of a surface-potential versus temperature curve" is used, it is often meant that measurement points of a potential-difference (between the first electrode and the second electrode) versus temperature difference (between the first electrode and the second electrode) is meant. Nevertheless, as in the invention it is not required to know the absolute temperature, but only to determine the slope of the surface-potential versus temperature curve, the latter curve has a clear relation with the first curve and is sufficient to obtain the slope.

So far, the description of the figures mainly dealt with the method of determining a charged particle concentration in an analyte in accordance with thermo-potentiometric measurement principle. However, the invention also relates to an electrochemical sensor comprising the electronic device of the invention, which can be used to carry out this method. Such electrochemical sensor may comprise measurement electrodes, such as ISFET's, EGFET's, and EIS capacitors.

Figure 5:
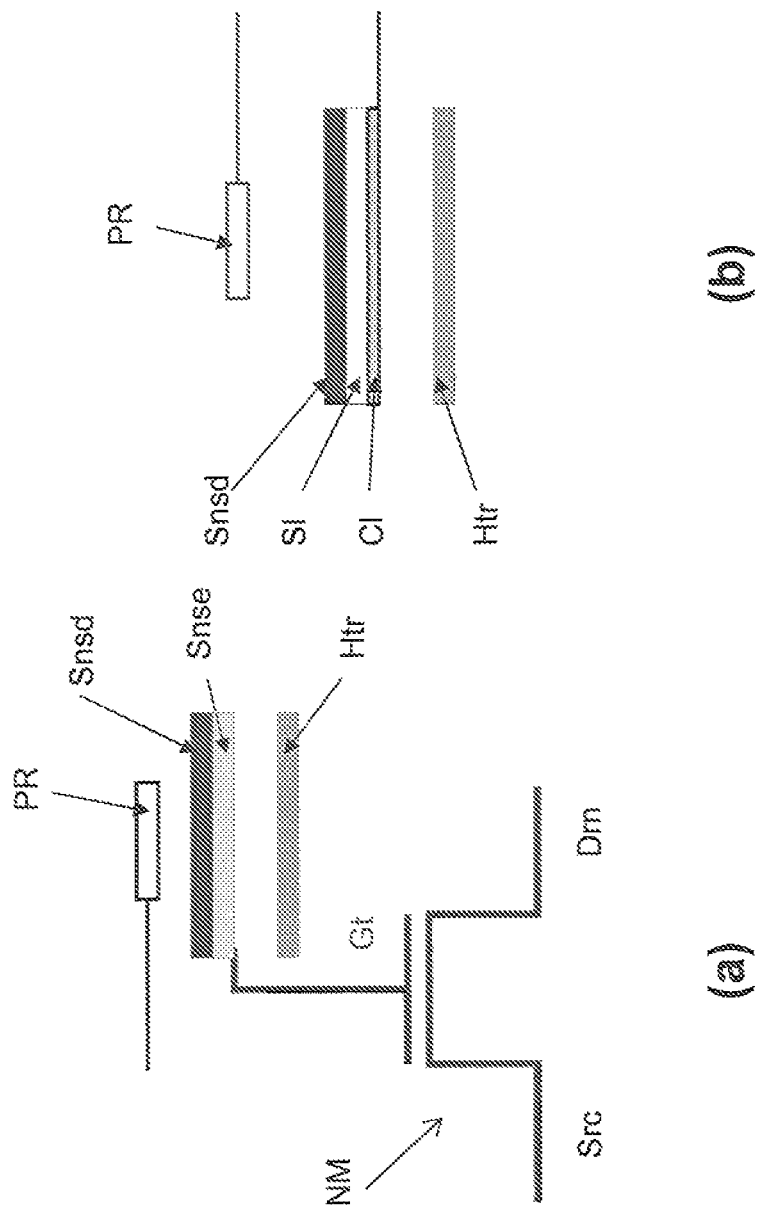
FIG. 5 shows two embodiments of a thermo-potentiometric electrochemical sensor with a pseudo-reference electrode to which the invention may be applied.

FIG. 5 shows two embodiments of a thermo-potentiometric electrochemical sensor with a pseudo-reference electrode to which the invention may be applied. FIG. 5(a) shows a so-called Extended Gate Field-Effect-Transistor (EGFET). FIG. 5(b) shows a so-called Electrolyte Insulator Semiconductor (EIS) structure.

Figure 7:
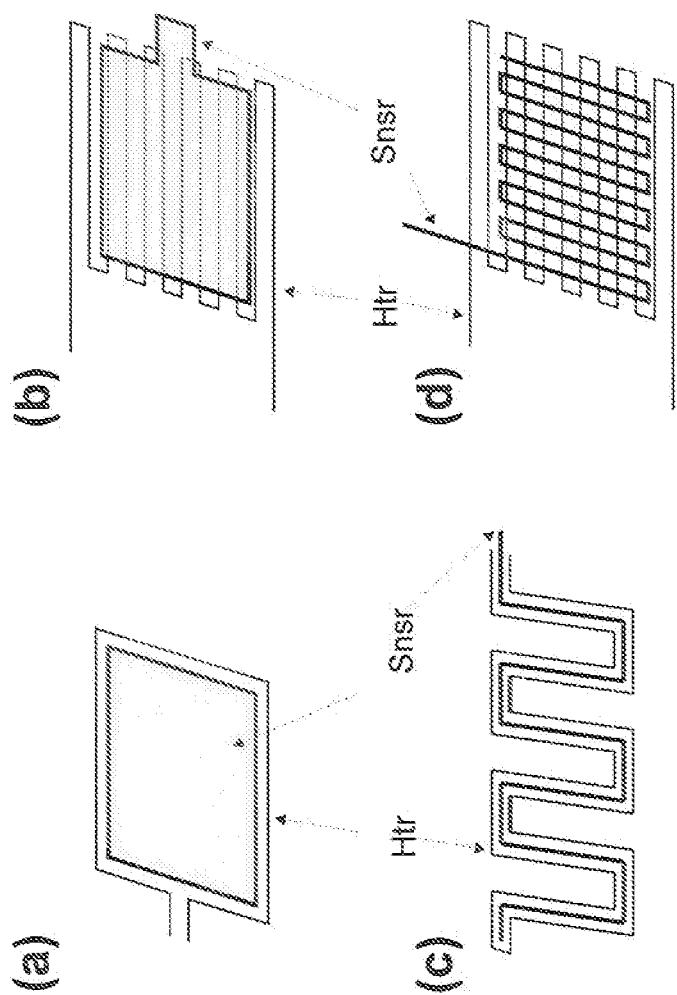
FIGS. 7(a) to 7(d) show four different sensor-heater arrangements that can be used in the electrochemical sensors of FIGS. 5 and 6.

Referring to FIG. 5(a). The sensor comprises a conventional transistor NM as tranducer having a source Src, a drain Drn, and a gate Gt, e.g. an NMOS transistor. The gate Gt of the transistor NM is connected to a sensor electrode Snse via standard metal interconnect 'wires'. On the sensor electrode Snse a sensor dielectric Snsd may be provided that is sensitive to certain ions. The sensor has been exemplified in a simplified way to facilitate understanding. A resistive heater Htr (temperature setting means) has been provided close, for example underneath, to the sensor electrode Snse and sensor dielectric Snsd. What is important is that the resistive heater Htr is provided such that it is thermally coupled to the sensor part for setting its temperature. Many variations are possible in this respect. Some of these variations are illustrated in FIG. 7. The transistor NM of the sensor has a floating gate, because the connection between gate Gt and sensor electrode Snse is not galvanically connected to any voltage source. Instead, it is surrounded by insulators such as the gate dielectric, sensor dielectric Snsd and interconnect dielectric. The working point of the sensor is controlled by a reference electrode, here a pseudo-reference electrode PR, in the analyte. The pseudo-reference electrode PR can be integrated with the EGFET, for example in the top metal layer.

The major advantage of the EGFET as compared to the ISFET is that the sensor electrode Snse is implemented in the top metal layer of the chip and thus 'far away' from the layer comprising the transistor NM. This reduces risk of contamination with, e.g. alkaline ions, such as $Na^+$. Moreover, it allows easy integration with standard CMOS processes.

Referring to FIG. 5(b), the Electrolyte Insulator Semiconductor structure comprises a conductive contact layer Cl (e.g. metal pad, silicide) onto which a silicon layer Sl is provided. On the silicon layer Sl a sensor dielectric Snsd is provided.

The stack is similar to a MOS (Metal Oxide Semiconductor) capacitor. It differs from there in that the dielectric/oxide is contacted by the analyte rather than by metal. The flat-band voltage of the EIS capacitor yields information on the pH-value/ion concentration of the analyte. It is determined by C-V (capacitance voltage) measurements or with a constant capacitance method. Both methods at least require a reference electrode to define the DC potential of the analyte and to modulate the analyte potential for the capacitance measurements. Again the temperature at the sensor dielectric/electrolyte interface is modulated with a resistive heater Htr near, for example underneath, the EIS layer stack. Temperature changes affect the surface potential that subsequently causes a shift in the flat-band voltage. Thus the surface potential is indirectly measured via the flat-band voltage. The reference electrode can be a simple pseudo-reference electrode PR for the same reason discussed with FIG. 5(a).

More information on the electrolyte-insulator semiconductor structure can be found in the following document:

Shoji Yoshida, Nobuyoshi Hara, and Katsuhisa Sugimoto, "Development of a Wide Range pH Sensor based on Electrolyte-Insulator Semiconductor Structure with Corrosion-Resistant $Al_2O_3$—$Ta_2O_5$ and $Al_2O_3$—$ZrO_2$ Double-Oxide Thin Films.", Journal of The Electrochemical Society, 151 (3) H53-H58 (2004) [REF4]. This document has been incorporated by reference in its entirety.

More information on C-V measurements can be found in the following document:

M. Klein, "CHARACTERIZATION OF ION-SENSITIVE LAYER SYSTEMS WITH A C(V) MEASUREMENT METHOD OPERATING AT CONSTANT CAPACITANCE.", Sensors and Actuators B1 (1-6): p 354-356, January 1990 [REF5]. This document has been incorporated by reference in its entirety.

Because of the special thermo-potentiometric measurement principle, the earlier described problems related to the reference electrode and calibration are no longer relevant (or at least to a much smaller degree) for the electrochemical sensor in accordance with this embodiment of the invention. In particular, the embodiments described here can be easily miniaturized and integrated into standard CMOS devices. Only minor additions to a standard processing scheme are necessary. Moreover, these modifications are after all conventional processing has been finished, and before dicing and packaging).

Figure 6:
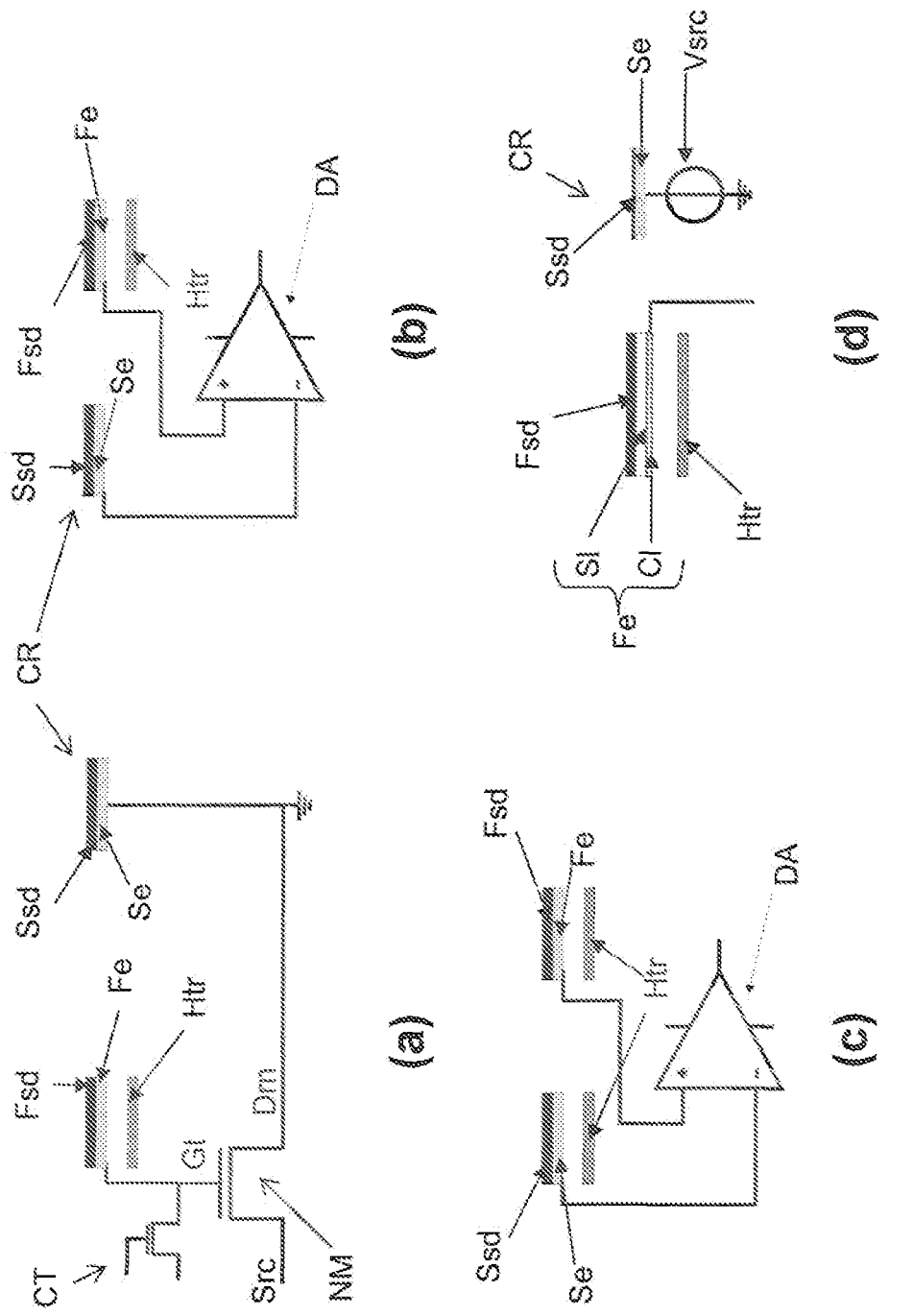
FIG. 6 shows four embodiments of a thermo-potentiometric electrochemical sensor without a reference electrode to which the invention may be applied.

FIG. 6 shows four embodiments of a thermo-potentiometric electrochemical sensor without a reference electrode to which the invention may be applied. FIG. 6(a) shows a so-called Extended Gate Field-Effect-Transistor (EGFET). It comprises a conventional transistor NM having a source Src, a drain Drn, and a gate Gt, i.e. an NMOS transistor. The gate Gt of the transistor NM is connected to a first electrode Fe via standard metal interconnect 'wires'. On the first electrode Fe a first sensor dielectric Fsd is provided that is sensitive to certain ions. The sensor has been exemplified in a simplified way to facilitate understanding of the invention. The electrochemical sensor further comprises a second electrode Se. On the second electrode Se a second sensor dielectric Ssd is provided. In order to form a capacitance, the second electrode Se is arranged to contact the analyte only through the second ion-sensitive dielectric Ssd, in operational use. In operational use, the first ion-sensitive dielectric Fsd forms a first interface with the analyte and the second ion-sensitive dielectric Ssd forms a second interface with the analyte.

The second electrode Se is connected to a fixed potential, e.g. ground. A resistive heater Htr (temperature setting means) has been provided close, for example underneath, to the first electrode Fe and first sensor dielectric Fsd. What is important is that the resistive heater Htr is provided such that it is thermally coupled to the first electrode Fe and the first sensor dielectric Fsd for setting a temperature of the first interface between the first sensor dielectric Fsd and the analyte in operational use. Providing the resistive heater Htr only near the first electrode Fe is a possible way of creating a temperature difference between said interfaces. Many variations are possible in this respect. Some of these variations are illustrated in FIG. 7. As explained earlier, in this implementation of a thermo-potentiometric electrochemical sensors it is no longer required setting the DC-potential of the analyte with a reference electrode (or a pseudo-reference electrode). Instead, it is only required to set a working-point of the transducer, i.e. the transistor NM. In this embodiment this is done by implementing a control transistor CT which is connected to the gate Gt for pre-setting its DC-potential. Such control transistor CT merely acts as a switching element receiving a DC-bias-voltage on its input and connected with its output to the gate and being controlled by a control signal on its control input (gate) for temporarily transferring this DC-bias-voltage to the gate Gt of NM (i.e. set the voltage on the floating gate). The DC-bias-voltage is chosen such that the measurement transistor NM operates in a proper operating point of its curve. It must be noted that the measurement signal which it receives on its gate is a transient voltage (modulated by the temperature) rather than a DC-voltage.

FIG. 6(b) shows a configuration having two measurement electrodes which are used in a differential way having only one heater. This embodiment will be discussed in as far as it differs from the embodiment in FIG. 6(a). Instead of using a transistor as transducer, a differential amplifier DA is used to measure the potential difference between the first electrode Fe and the second electrode SE. The resistive heater Htr is provided near the first electrode Fe only. The first electrode Fe and the second electrode Se are connected to inputs of the differential amplifier DA. This embodiment may be used as follows. The right sensor is heated/cooled creating a voltage difference between both amplifier inputs. Any (constant) offset between the inputs is not relevant for the measurement, because the measurement signal is conveyed in the "additional" difference resulting from the heating/cooling of the right sensor.

In the embodiments of FIG. 6(a) and FIG. 6(b) the second electrode Se together with the second ion-sensitive dielectric Ssd may be considered as a capacitive reference CR for the first electrode Fe and the first ion-sensitive dielectric Fsd. It is possible to provide a control transistor/switching element for each input of the differential amplifier in the same way as illustrated in FIG. 6(a). Such element can be used to preset the DC-voltages of the inputs (and thereby the electrodes).

FIG. 6(c) shows a configuration having two measurement electrodes which are used in a differential way having two resistive heaters Htr. This embodiment will be discussed in as far as it differs from the embodiment in FIG. 6(b). The main difference is that this embodiment is provided with a heater Htr at each electrode, i.e. the temperature of both electrodes is controlled (but differently) for creating the required temperature difference. This embodiment may be used as follows. First, the temperature of the first electrode Fe is varied while the temperature of the second electrode Se is kept constant (same operation as for simple configuration with only one heater). Measurements are done during this temperature variation, i.e. the potential difference between the first electrode Fe and the second electrode Se is measured for the different temperatures of the first electrode providing the measurement points of the potential-temperature curve. This provides a first slope. Then, the same measurement is done varying the temperature of the second electrode Se while keeping the temperature of the first electrode Fe constant. This provides a second slope. Both obtained slopes are then averaged which may remove any systematic measurement error originating from the heating of a single sensor. Consequently, the measurement accuracy may be increased. In this embodiment it is more difficult to indicate a capacitive reference, because both electrode configurations have a similar function. It could be argued that the respective electrodes alternatingly act as a reference and a measurement electrode, respectively. It is possible to provide a control transistor/switching element for each input of the differential amplifier in the same way as illustrated in FIG. 6($a$). Such element can be used to preset the DC-voltages of the inputs (and thereby the electrodes).

FIG. 6($d$) shows a so-called Electrolyte Insulator Semiconductor (EIS) structure. The Electrolyte Insulator Semiconductor structure comprises a first electrode Fe comprising a conductive contact layer Cl (e.g. metal pad, silicide) onto which a silicon layer Sl is provided. Alternatively, it may be a germanium layer, a silicon-germanium layer, a III-V semiconductor compound, a II-VI semiconductor compound or any other kind of semiconductor compound. On the silicon layer Sl a sensor dielectric Snsd is provided. The stack is similar to a MOS (Metal Oxide Semiconductor) capacitor. It differs there from in that the dielectric/oxide is contacted by the analyte rather than by metal. The flat-band voltage of the EIS capacitor yields information on the pH-value/ion concentration of the analyte. It is determined by C-V (capacitance voltage) measurements or with a constant capacitance method. Normally, both methods require a reference electrode and an electrode to modulate the analyte potential for the capacitance measurements. In this embodiment of the electrochemical sensor, however, such reference electrode is no longer required. Instead, a capacitive reference CR similar to the previous embodiments is provided. The capacitive reference CR comprises a second electrode Se provided with a second ion-sensitive dielectric Ssd thereon. In order to form a capacitance, the second electrode Se is arranged to contact the analyte only through the second ion-sensitive dielectric Ssd, in operational use. If leakage is sufficiently small the analyte potential can be set via this capacitive reference, this is done via a voltage source Vsrc connected between the capacitive reference CR and ground in FIG. 6($d$) (the overall measurement time must be smaller than the time constant of the change in DC voltage caused by the leakage). Moreover, the AC modulation for the capacitance measurement is applied via the same capacitive reference CR. The DC potential of the analyte is set as follows. When the voltage of the voltage source Vsrc is switched to a different voltage the voltage over the capacitive reference CR changes and thus the potential of the analyte 100 accordingly (the first capacitor $C_{fe}$ and the second capacitor $C_{se}$ that are connected in series via the analyte form a capacitive voltage divider). However, this only applies under ideal conditions without any leakage. In case of leakage the DC potential of the analyte 100 gradually changes due to charge/discharge of the reference capacitor. It is important that in that case the time constant of this charge/discharge must be much higher than the duration of the measurements. In case of the EIS device the (DC) voltage is varied via the reference electrode and also the (sinusoidal) modulation is applied.

Again the temperature at the first dielectric Fsd/first interface is modulated with a resistive heater Htr near, for example underneath, the EIS layer stack. Temperature changes (implying also a change in the temperature difference between the first interface and the second interface) affect the surface potential that subsequently causes a shift in the flat-band voltage. Thus the surface potential is indirectly measured via the flat-band voltage.

More information on the electrolyte-insulator semiconductor structure can be found in the earlier cited document from Shoji Yoshida et al. More information on C-V measurements can be found in the earlier cited document from M. Klein.

Because of the special thermo-potentiometric measurement principle the earlier described problems related to the reference electrode and calibration are no longer relevant (or at least to a much smaller degree) for the electrochemical sensor in accordance with these embodiments of the invention. In particular, the embodiments described here can be easily miniaturized and integrated into standard CMOS devices. Only minor additions to a standard processing scheme are necessary. Moreover, these modifications are after all conventional processing has been finished, and before dicing and packaging).

FIGS. 7($a$) to 7($d$) show four different sensor-heater arrangements that can be used in the electrochemical sensors of FIGS. 5 and 6. All figures are simplified, in particular for the electrochemical sensor. For the sensor only the sensor electrodes are shown. In FIG. 7($a$) the sensor Snsr is arranged as a large pad, whereas the resistive heater Htr is arranged (in a same plane) around the periphery of the pad. In FIG. 7($b$) the resistive heater Htr is arranged under the sensor pad Snsr in the form of a meander. This configuration ensures a more uniform temperature of the sensor. In FIG. 7($c$) the sensor Snsr is arranged as a meander structure, and the resistive heater Htr is arranged, in a same plane, as a meander structure on both sides of the sensor Snsr in a river-routing fashion. In FIG. 7($d$) the sensor Snsr is arranged as a meander structure. The resistive heater Htr is arranged below the sensor Snsr as a meander structure in a 90°-rotated. The actual arrangement of heater Htr and sensor Snsr may considerably affect the temperature uniformity of the sensor. The person skilled in the art may easily come up with further variations of the sensor Snsr and heater Htr. In any case, what is important is that the resistive heater Htr (temperature settings means) is thermally coupled to the sensor Snsr for enabling the setting of the sensor (interface) temperature.

The sensor/heater configurations shows in FIGS. 7($a$) to 7($d$) are easy to manufacture and efficient in heat transfer (in particular the embodiments FIGS. 7($b$) and 7($d$)). Nevertheless, these configuration also suffer from a disadvantage, which, as the inventor has discovered, is caused by the large capacitance (i.e. there is a large capacitive coupling) between the resistive heater Htr and the sensor electrode Snsr. This causes a capacitive charging of the sensor electrode Snsr if a voltage or current pulse is applied to the resistive heater Htr (which is for example the case in thermo-potentiometric measurements where the temperature needs to be modulated). Depending on the actual sensor/heater configuration and the parasitic capacitance there between the induced voltage can be as high as half the amplitude of the heat pulse.

Unfortunately, the sensor signal can be considerably smaller than the heat pulse amplitude (for example from about 20 μV to several hundreds of millivolt's in case of thermo-potentiometric electrochemical sensors) versus several Volt for the induced pulse (artifact) because of the capacitive charging effect). Therefore the signal may be very difficult to detect.

In principle the measured signal (sensor electrode signal+ capacitive voltage) can be corrected for the heat pulse artifact by subtracting it (if heat pulse amplitude and (parasitic)

capacitances of the configuration are known or by proper calibration). However, errors may be introduced in this approach and the electrochemical sensor becomes more complex. More importantly, the high amplitude of the capacitive voltage can overload the transducer, which is connected to the sensor electrode (FET, differential amplifier, etc.), that converts the sensor electrode signal. Reducing the sensitivity or gain will solve this problem, which is at the cost of resolution and accuracy and therefore not an attractive solution. Alternatively, the sensor electrode signal could be measured after occurring of the heat pulse. The approach requires the controlled temperature to remain stable until capacitive artifacts have decayed and the transducer/amplifier has recovered from overload. These conditions can be only achieved if the heat capacitance of the sample is large enough and heat dissipation is low, i.e. high heating power is required (bad for stand alone, battery powered applications).

The invention proposes a solution for reducing/preventing the capacitive charging of the sensor Snsr (by the resistive heater Htr) during temperature modulation (heating). The main feature of the invention is to provide signal integrity protection to the heater Htr instead of the clever ad-hoc solutions discussed above. Two main variants of the signal integrity protection are discussed. The first main variant is based on a special driving pattern for the resistive heater, the second main variant comprises the provision of a shield around the resistive heater. The main variants and their embodiments will be discussed hereinafter.

FIGS. 8(a) to 8(d) show sensor-heater arrangements in accordance with a first group of embodiments of the invention. FIG. 9(a) shows a graph explaining the transient behavior of the potentials of the terminals of the resistive heater in the embodiment of FIGS. 8(a) and 8(b). FIG. 9(b) shows a graph explaining the transient behavior of the voltage as applied to the resistive heater as used in the embodiment of FIGS. 8(c) and 8(d).

In FIGS. 8(a) and 8(b) the sensor heater configuration is the same as in FIGS. 7(a) and 7(b), respectively. The resistive heater Htr has two terminals $+U_H$, $-U_H$. The signal integrity protection in this embodiment comprises a driver circuit (not shown) for the resistive heater Htr for applying synchronous voltage pulses with same amplitude but opposite polarity to the heater contacts $+U_H/-U_H$ as illustrated in FIG. 9(a). Here there are different options. In the example of FIG. 8(a)/9(a) one terminal $+U_H$ is switched between a high level LH (for example Vdd) to a mid-level LM (for example GND). The other terminal $-U_H$ is switched between the mid-level LM and a low level LL (for example -Vdd). Alternatively, one terminal may be switched between Vdd and ½Vdd, and the other between ½Vdd and GND. In any case the voltage transients are opposite and with equal amplitude. Applying voltage pulses (but also current pulse works fine) to the resistive heater Htr is a convenient way of controlling heat generated by it. The power generated can be varied by varying the pulse amplitude, frequency, but also the pulse duty cycle. If the sensor electrode/heater configuration is symmetric (which is the case for the embodiments in both FIG. 8(a) and FIG. 8(b)) the capacitive voltages fully cancel each other on the sensor electrode Snsr. With symmetry it is meant that the capacitive coupling between the sensor electrode Snsr and the resistive heater Htr on one path from one terminal towards a heater mid-point MP equals the capacitive coupling on the other path from the other terminal towards the heater mid-point MP.

It must be noted that the potential at the midpoint MP remains GND if the paths from both terminals to the midpoint MP have the same resistance, which results in a same voltage drop (opposite polarity). More symmetry leads to a better cancelling effect and thereby less capacitive charging. Less symmetry also leads to a cancelling effect, but to a lesser extent. The cancelling effect achieved in these two examples is also being referred to as spatial-averaging. Spatial averaging works irrespective of the voltage on the sensor electrode since the same amount of positive charge and negative charge is induced on the electrode and is "short-circuited" by the electrode.

In FIGS. 8(c) and 8(d) the sensor heater configuration is the same as in FIGS. 8(a) and 8(b), respectively. Also in these embodiments voltage pulses (or current pulses) are applied. However, here a time-averaging effect is used. One terminal is connected to a baseline potential BL, such as ground, GND. The other terminal is switched at high frequency (again by a driver circuit forming part of the signal integrity protection) symmetrically around this potential in accordance with FIG. 9(b). It may be switched between a high level LH, such as Vdd, and a low level LL, such as -Vdd. Alternatively, it may be switched between Vdd and GND (the baseline BL is then at ½ Vdd). The high-frequency pulses on the resistive heater Htr induce high-frequency modulations on the sensor electrode signal. The high-frequency modulations on the sensor electrode signal are filtered out with a low-pass filter LPF, which creates a time-averaging effect on the sensor electrode signal. The output of the low-pass filter LPF can be fed to a tranducer for measuring the averaged sensor electrode signal. In other words, the sensor signal is conveyed in the averaged measurement signal, i.e. capacitive artifacts cancel out due to opposite polarity). As far as the time-averaging embodiments are concerned, it must be noted that the low-pass filter LPF is provided between the sensor electrode Snse and the gate Gt in FIGS. 5(a) en 6(a). In FIGS. 5(b) and 6(d) the low-pass filter LPF is provided directly after the conductive layer Cl.

In case of an EIS configuration the situation is a bit more complex. In EIS configurations there is another AC voltage (required for the C-V measurements), the resistive heater pulse frequency must be much higher than the probe frequency and the filter must block the heater induced pulse and at the same time let through the probe signal. Finally, in FIGS. 6(b) and 6(c) the low-pass filter LPF is provided between the first electrode Fe and the differential amplifier DA (in fact, in FIG. 6(c) it is provided twice, one for each differential amplifier input).

All embodiments illustrated in FIGS. 8(a) to 8(d) only involve a specific pulse pattern and wiring of the resistive heater Htr. Therefore, they can be implemented in a standard CMOS process without additional steps or special process modules.

FIGS. 10(a) to 10(e) show sensor-heater arrangements in accordance with a second group of embodiments of the invention. In all embodiments illustrated in this figure the resistive heater Htr is provided with a conductive shield Shld that is connected to a fixed reference potential (for example ground level). The shield Shld is a good signal integrity protection. Ideally, the capacitive voltage is only induced in the shield Shld (by the resistive heater Htr) and short-circuited to ground thus the electric field around the sensor does not change. FIGS. 10(a) and 10(b) depict two planar sensor-shield-heater arrangements (as in FIGS. 7(a) and 7(c)) with the shield Shld implemented as 'wire' conductor surrounding the sensor electrode Snsr (square-shaped pad in FIG. 10(a) and meander-shaped in FIG. 10(b)). These embodiments are easy to implement (only one metal layer needed), but the shielding efficiency is reduced because of fringe fields which run from the resistive heater Htr to the sensor electrode Snsr (wider shield wire increases performance, but this is at the cost of area and increased heating power).

FIGS. 10(c) and 10(d) depict similar configurations as in FIGS. 7(b) and 7(d), with the important difference that the shield Shld, a grounded plane, is provided in a layer between the resistive heater Htr and the sensor electrode Snsr, i.e. they constitute three-layer stacks, which have a high shielding efficiency. Fringe fields are efficiently suppressed if the shield Shld overlaps the heater and sensor area. The embodiments in FIGS. 10(c) and 10(d) require a (CMOS) process technology with at least three metal layers. In case of a process technology with more than 3 metal layers no extra processing steps are required, all steps are done by design. The resistive heater Htr is implemented in Metal1 as thin a meander line. On top of this layer (Metal2) a shield plane Shld is processed that fully covers the resistive heater Htr with some overlap on all sides. The shield Shld is connected to ground or another fixed and stable reference potential. The electrode layer Snse of the sensor electrode Snsr is made in Metal3 (top metal layer, often used for bondpads) with the sensor dielectric Snsd or other sensitive material provided on top, as illustrated in FIG. 10(e).

Figure 8:
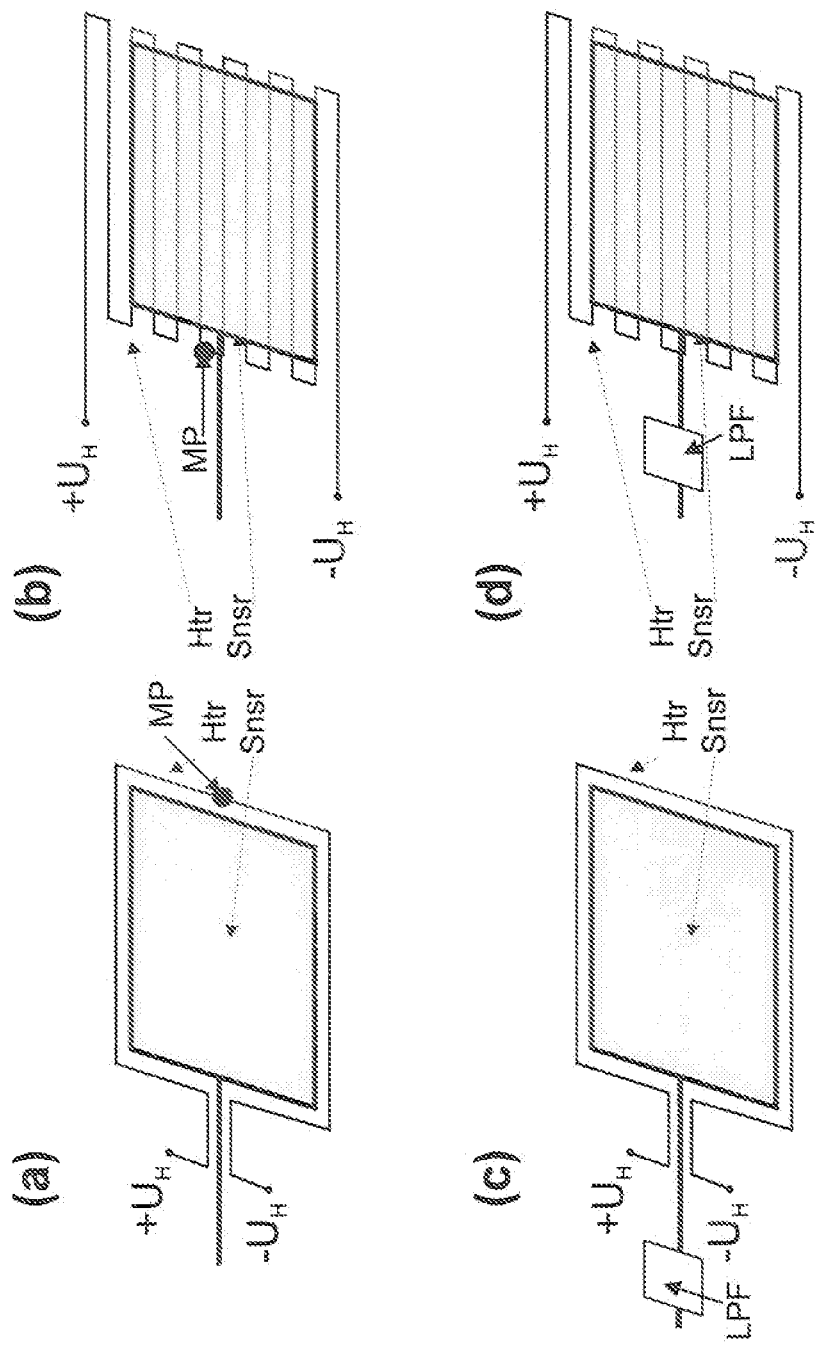
FIGS. 8(a) to 8(d) show sensor-heater arrangements in accordance with a first group of embodiments of the invention.
Figure 9:
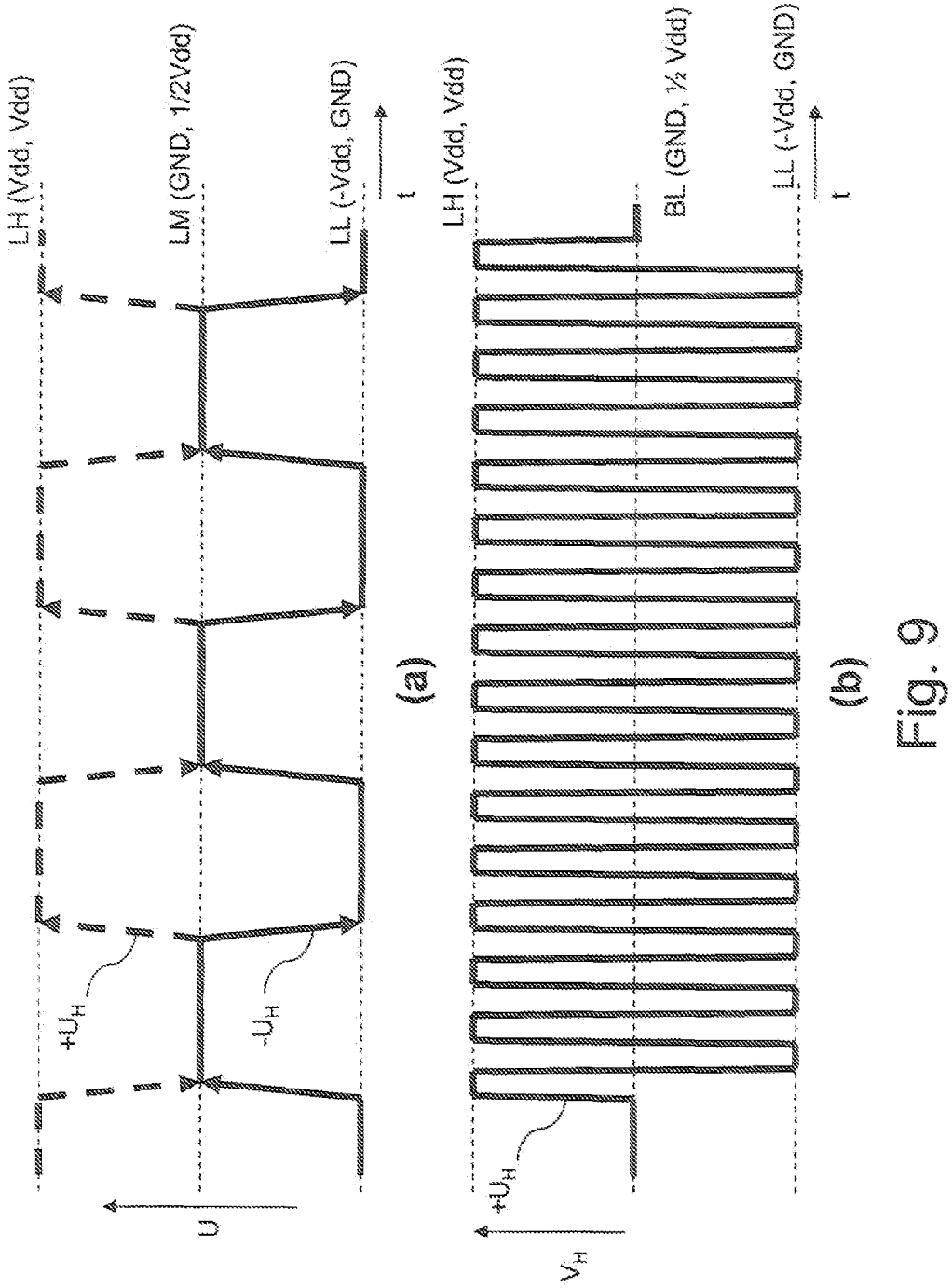
FIG. 9(a) shows a graph explaining the transient behavior of the potentials of the terminals of the resistive heater in the embodiment of FIGS. 8(a) and 8(b)
FIG. 9(b) shows a graph explaining the transient behavior of the voltage as applied to the resistive heater as used in the embodiment of FIGS. 8(c) and 8(d), and FIGS. 10(a) to 10(e) show sensor-heater arrangements in accordance with a second group of embodiments of the invention.
Figure 10:
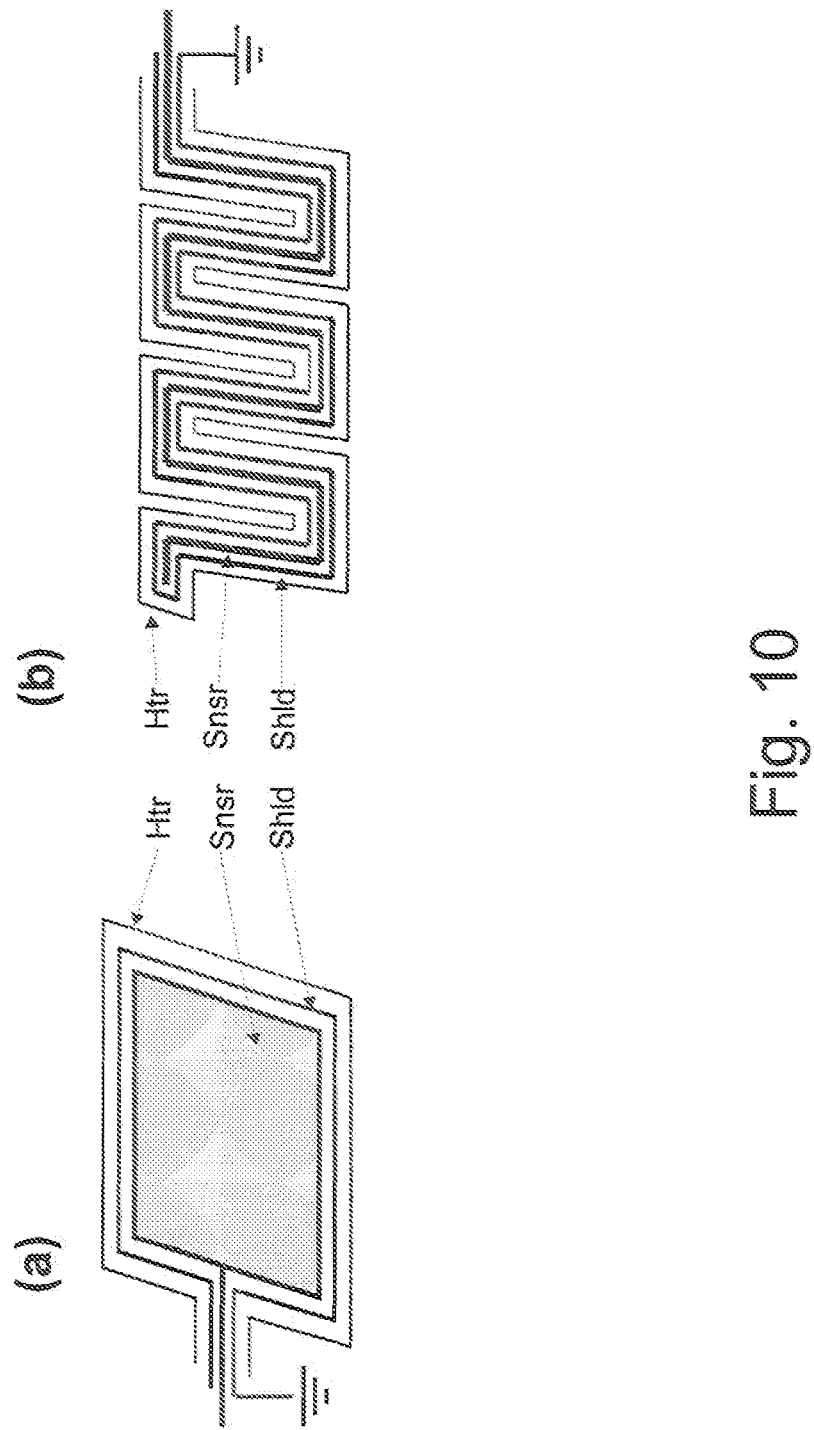
Figure 10:
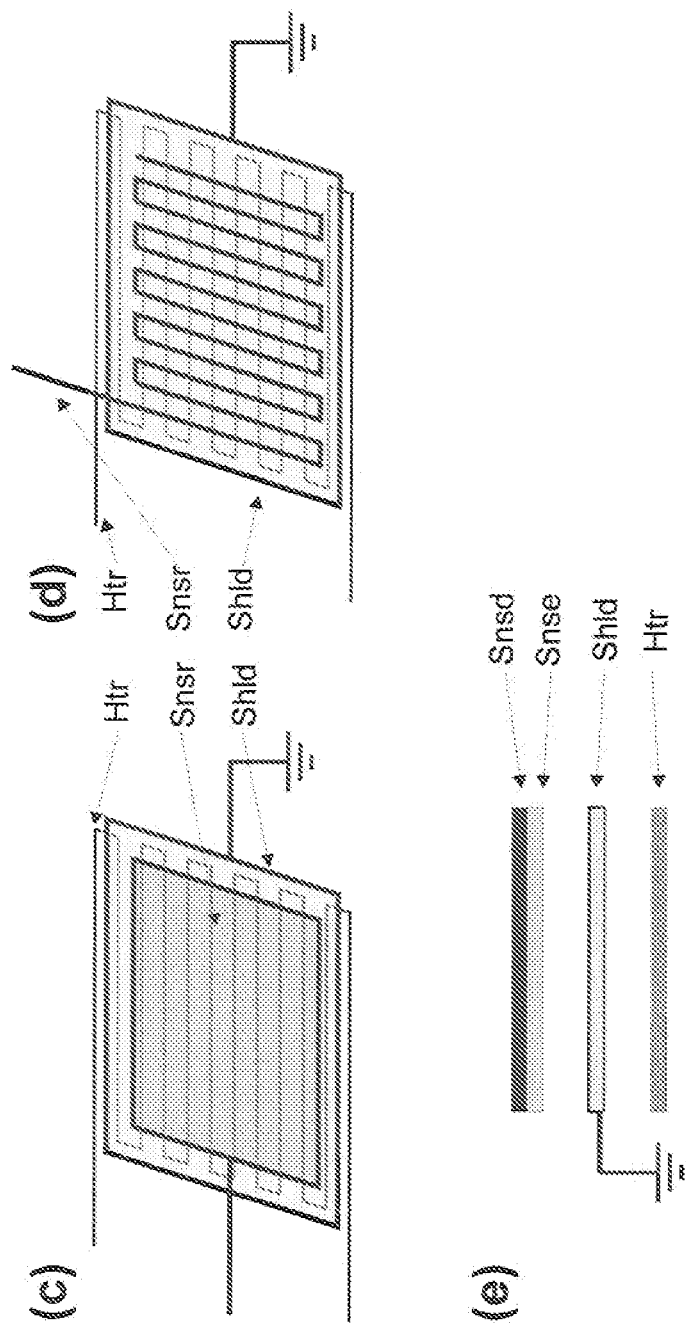

It must be noted that in order to reduce the capacitive charging even more, i.e. minimize heating artifacts, two variants discussed in FIGS. 8 and 10 can be advantageously combined.

The invention thus provides an electronic device for measuring and/or controlling a property of an analyte 100. The electronic device comprises: i) an electrode Snsr forming an interface with the analyte 100 in which the electrode Snsr is immersed in operational use, the interface having an interface temperature T, and ii) a resistive heater Htr being thermally and capacitively coupled to the electrode Snsr, the resistive heater Htr being configured for setting the interface temperature T by controlling a current through the resistive heater Htr. The resistive heater Htr is provided with signal integrity protection for reducing the capacitive charging between the resistive heater Htr and the electrode Snsr if the current through the resistive heater Htr is modulated. The invention further provides an electrochemical sensor for determining a charged particle concentration in the analyte 100 using the thermo-potentiometric principle, the electrochemical sensor comprising such electronic device. The invention also provides an RFID tag and a semiconductor device comprising such electrochemical sensor. The effect of the feature of the invention is that the capacitive charging effect between the resistive heater and the electrode is reduced by the signal integrity protection.

The invention may be applied in various application areas. For example, the invention may be applied in any electronic device having an electrode in close proximity with a resistive heater. The invention is particularly applicable to integrated (miniature) chemical sensors (pH sensors, ion concentrations sensors, bio molecule sensors) that uses the thermo-potentiometric principle for analyte detection. The invention reduces/prevents capacitive charging of the sensor (and thus measurement errors) during modulation of the analyte temperature.

Various variations of the electronic device and electrochemical sensor in accordance with the invention are possible and do not depart from the scope of the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage. Throughout the Figures, similar or corresponding features are indicated by same reference numerals or labels.

The invention claimed is:

1. An electronic semiconductor device for measuring and/or controlling a property of an analyte, the electronic semiconductor device comprising:
    an electrode, within the electronic semiconductor device, forming an interface with the analyte in which the electrode is immersed in operational use, the interface having an interface temperature (T), and
    a resistive heater, within the electronic semiconductor device, being capacitively coupled to the electrode, the resistive heater being configured for setting the interface temperature (T) based on a current passed through the resistive heater,
    wherein the electronic semiconductor device includes a signal integrity protection module for reducing the capacitive charging of the electrode by the resistive heater,
    wherein the resistive heater comprises two terminals and a conductive path between the terminals; and
    wherein the signal integrity protection further comprises a conductive shield, within the electronic semiconductor device, arranged between the resistive heater and the electrode, wherein the conductive shield is connected to a fixed reference potential.

2. The electronic device as claimed in claim 1, wherein the signal integrity protection comprises a driver circuit coupled to the terminals for controlling the current through the conductive path.

3. The electronic device as claimed in claim 2, wherein the driver circuit is configured for applying voltage pulses to the two terminals of the resistive heater to obtain the current.

4. The electronic device as claimed in claim 3, wherein the driver circuit is configured for applying the voltage pulses such that respective potentials of the two terminals are switched synchronously and oppositely with respect to each other.

5. The electronic device as claimed in claim 4, wherein the respective potentials of the terminals are switched with equal amplitude.

6. The electronic device as claimed in claim 3, wherein the electrode has an electrode potential, and wherein the driver circuit is configured for applying the voltage pulses such that a potential of one of said terminals, is switched symmetrically around a baseline reference potential while the other one of said terminals is connected to said baseline reference potential and at high-frequency to obtain an electrode signal with high-frequency-modulations, wherein the signal integrity protection further comprises a low-pass filter connected to the electrode and being configured for filtering the high-frequency modulations in the electrode signal.

7. The electronic device as claimed in claim 1, wherein the electrode and the resistive heater are arranged symmetrically with respect to each other to obtain equal impedances on both paths from each selective one of said terminals to a midpoint of the resistive heater.

8. An electrochemical sensor for determining a charged particle concentration in the analyte using the thermo-potentiometric principle, the electrochemical sensor comprising the electronic device of claim 1.

9. The electrochemical sensor as claimed in claim 8, wherein the electrode is a sensor electrode for measuring a surface-potential at the interface, wherein the electrochemical sensor further comprises a control means for measuring the surface-potential at at least two different temperatures of the interface to obtain at least two measurement points of a surface-potential versus interface-temperature curve, wherein the resistive heater is arranged for setting the interface temperature at the at least two different values.

10. The electrochemical sensor as claimed in claim 8, wherein the electrode is a sensor electrode comprising: i) a first electrode with a first ion-sensitive dielectric provided thereon, the first electrode being arranged for contacting the analyte via the first ion-sensitive dielectric to obtain a first interface between the first ion-sensitive dielectric and the analyte, and ii) a second electrode with a second ion-sensitive dielectric provided thereon, the second electrode being arranged for contacting the analyte via the second ion-sensitive dielectric to obtain a second interface between the second ion-sensitive dielectric and the analyte,
wherein the electrochemical sensor further comprises a control means for measuring a potential difference between the first electrode and the second electrode at at least two different values of a temperature difference between the first interface and the second interface to obtain at least two measurement points of a surface-potential versus interface-temperature curve, and
wherein the resistive heater is arranged for setting the temperature difference at the at least two different values.

11. The electrochemical sensor as claimed in claim 9, wherein the control means comprises a controller, the controller being coupled to the sensor electrode and being arranged for initiating the measuring of the surface-potential with the sensor electrode at the at least two different values.

12. A semiconductor device comprising the electrochemical sensor as claimed in claim 8, the semiconductor device comprising a semiconductor body and at least one interconnect layer, wherein the sensor electrode is located in the at least one interconnect layer, and wherein the control means is located in the semiconductor body and/or the at least one interconnect layer.

13. An RF-ID tag comprising the electrochemical sensor as claimed in claim 8.

* * * * *